US006207168B1

(12) United States Patent
Aurelian

(10) Patent No.: US 6,207,168 B1
(45) Date of Patent: *Mar. 27, 2001

(54) VACCINE COMPOSITION FOR HERPES SIMPLEX VIRUS AND METHODS OF USING

(75) Inventor: Laure Aurelian, Baltimore, MD (US)

(73) Assignee: University of Maryland at Baltimore, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/413,512

(22) Filed: Oct. 6, 1999

Related U.S. Application Data

(62) Division of application No. 09/088,388, filed on Jan. 16, 1998, now Pat. No. 6,054,131.

(51) Int. Cl.$^7$ .......................... A61K 39/245; A61K 39/12
(52) U.S. Cl. ..................... 424/231.1; 424/229.1; 424/204.1; 424/199.1; 424/205.1; 435/320.1; 435/235.1; 536/23.72
(58) Field of Search ............................. 424/199.1, 204.1, 424/205.1, 229.1, 231.1; 435/320.1, 325.1; 536/23.72

(56) References Cited

U.S. PATENT DOCUMENTS

| | | |
|---|---|---|
| 4,347,127 | 8/1982 | Duttera et al. . |
| 4,452,734 | 6/1984 | Larson et al. . |
| 4,554,159 | 11/1985 | Roizman et al. . |
| 5,171,568 | 12/1992 | Burke et al. . |
| 5,219,567 | 6/1993 | Skinner et al. . |

OTHER PUBLICATIONS

Smith, et al. The PK Domain of the Large Subunit of Herpes Simplex Virus Type 2 Ribonucleotide Reductase (ICP10) is Required for Immediate–Early Gene Expression and Virus Growth. *Journal of Virology*. Nov. 1998, vol. 72, No. 11, pp. 9131–9141.
M. Waxhsman, L. Aurelian, J.C.R. Hunter, M.E. Perkus Expression of herpes simplex virus glycoprotein D on Bioscience Reports, 8, 323–334, 1988.
M. Wachsman, J.H. Luo, L. Aurelian, E. Paoletti Protection from herpes simplex virus type 2 is associ Vaccine, 10, 447–453, 1992.
M. Wachsman, L. Aurelian, C.C. Smith, M.E. Perkus and Regulation of Expression of herpes simples virus (HSV Journal of Infectious Diseases 159, 625–634, 1989.
Mary_Ann Mullen, Dolores M. Ciufo, Gary S. Hayward Mapping of intracellular localization domains and evi Journal of Virology 68, 3250–3266, 1994.
Stephen A. Rice, Melissa C. Long, Vivian Lam Charlott RNA polymerase II is aberantly phosphorylated and loc Journal of Virology 68, 988–1001 1994.
May Ann Hardwicke, Rozanne M. Sandri_Goldin The herpes simplex virus regulatory protein IPC27 Journal of Virology 68, 4797–4810, 1994.

Peter O'Hare and Gary S. Hayward Evidence for a direct role for both the 175,000 and Journal of Virology, 53, 751–760, 1985.
Chu–Pei Feng, Michael Kulka, Cynthia Smith and Laure Herpes simplex virus–mediated activation of human imm Antisense and Nucleic Acid Drug Development 6, 25–351996.
Bruce C. Strnad and Laure Aurelian Proteins of herpesvirus type 2 Virology, 73, 244–258, 1976.
Robert W. Honess, Bernard Roizman Regulation of herprsvirus macromolecular synthesis Journal of Virology, 14, 8–19, 1974.
Kent W. Wilcox, Alexander Kohn, Elena Sklyanskaya and Herpes simplex virus phosphoproteins I. Phosphate cyc Journal of Virology 33, 167–182, 1980.
Richard A.F. Dixon and Priscilla A. Schaffer Fine–structure mapping and functional analysis of tem Journal of Virology 36, 189–203, 1980.
Lorna A. Samaniego, Arthus L. Webb and Neal A Deluca Functional interactions between herpes simplex virus Journal of Virology, 69, 5705–5715, 1995.
Rosario Leopardi and Bernard Roizman Functional interaction and colocalization of the herp Proceedings National Acadamy Science 93, 4572–76, 1996.
Stephen A Rice, Melissa C. Long, Vivian Lam, Priscill Herpes simplex virus immediate–early protein ICP22 is Journal of Virology, 69, 5550–59, 1995.
Alice M. McCarthy, Linda McMahan and Priscilla A Scha Herpes simplex virus type I Icp27 deletion nutants Journal of Virology, 63, 18–27, 1989.
Wendy R. Sacks, Constance C. Greene, Doris P. Aschman Herpes simplex virus type I ICP27 is an essential reg Journal of Virology 55, 796–805 1985.
Rolf Ingemarson, Hilkka Lankinen The herpes simplex virus type 1 robonucleotide reduct Virology, 156, 417–422, 1987.
C.C. Smith, M. Kulka, J.P. Wymer, T.D. Chung and L. A Expression of the large subunit of herpex simplex vir Journal General Virology, 73, 1417–1428, 1992.
Peir Franco Pignatti, Enzo Cassai, Guerrino Meneguzzi Herpes simplex virus DNA isolation from infected cell Virology 93, 260–264, 1979.
David J. Goldstein and Sandra K. Weller Factor(s) present in herpes simplex virus type 1–infe Virology 166, 41–51, 1988.
James P. Wymer, Theodore D. Chung, Yung–Nien Chang, Identification of immediate–early–type cis–response Journal of Virology 63, 2773–2784, 1989.
Theodore D. Chung, Jianhua Luo, James P. Wymer, Cynthi Leucine repeats in the large subunit of herpes simplex Journal of General Virology 72, 1139–1144, 1991.

(List continued on next page.)

Primary Examiner—Laurie Scheiner
(74) Attorney, Agent, or Firm—Gilberto M. Villacorta; Corinne M. Pouliquen; Pepper Hamilton LLP

(57) ABSTRACT

The present invention discloses a new vaccine composition for Herpes Simplex comprising a whole live HSV-2 virus having the oncogene deleted. Methods of using the vaccine composition are also included.

18 Claims, 13 Drawing Sheets

OTHER PUBLICATIONS

Figure 1:
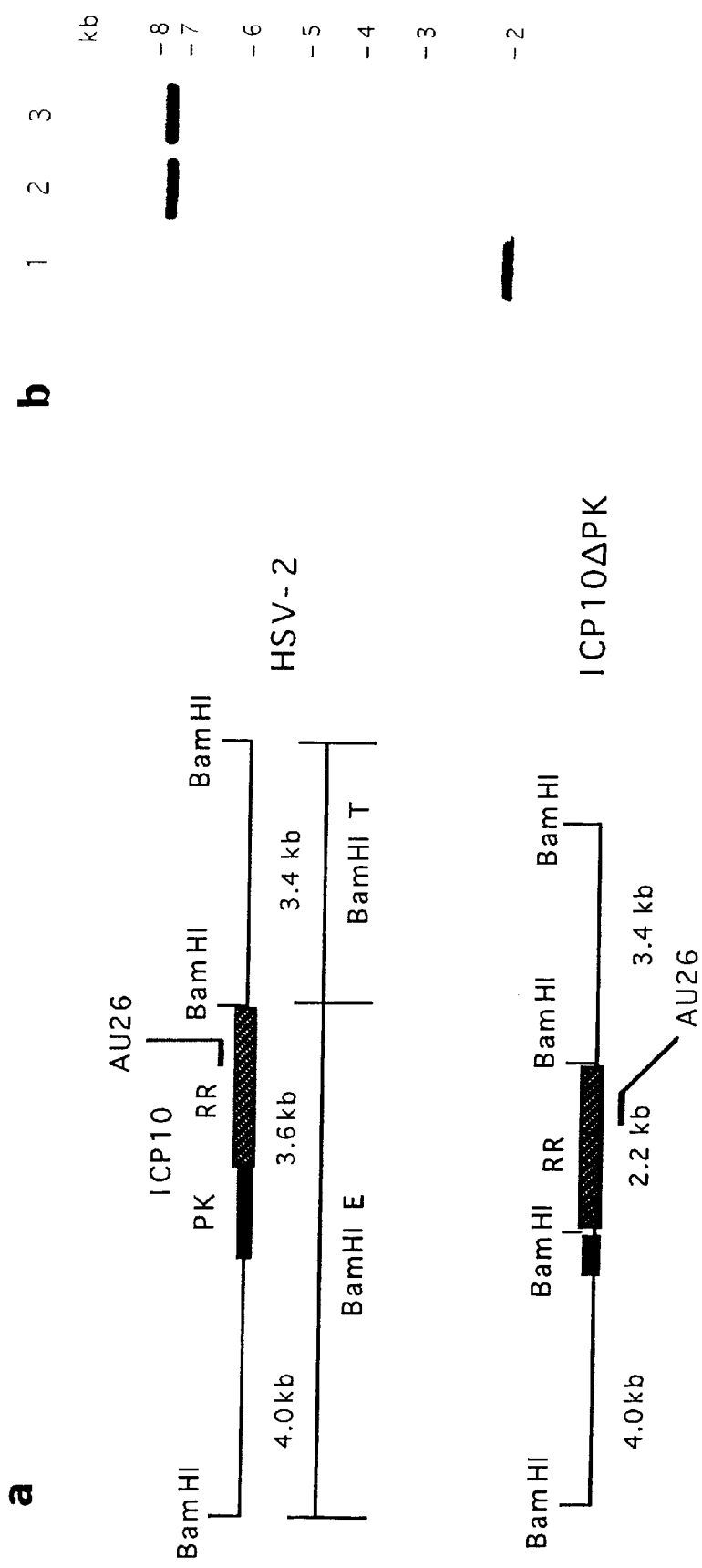

Laure Aurelian 27 Herpes simplex viruses. 473–499, unnamed, undated.

L. Aurelian, P. Tarzano, C.C. Smith, T. Chung, A. Sham Amino–terminal epitope of herpes simplex virus type 2 Cancer cells 7 187–191, 1989.

Ann M. Arvin, Charles G. Prober Herpes simplex virus type 2—a persistent problem New England Journal Medicine, Oct. 16, 1997, 1158–9, v. 337.

Rhoda L. Ashley, Julie Dalessio, Sandra Burchett, Zane Herpes simplex virus–w (HSV) type–specific antibody co Journal Clinical Investigation, 90, 511–14, 1992.

Laure Aurelian Herpes simplex 73–100, unnamed, undated.

Douglas T. Fleming, Geraldine M. McQuillan, Robert E. Herpes simplex virus type 2 in the United States 1976 New England Journal of Medicine 337, 1105–1111, 1997.

Richard J. Whitley, John W. Gnann, Jr. Acyclovir: a decade later New England Journal of Medicine, 327, 782–789, 1992.

Laure Aurelian Preface, Herpesviruses, the immune system, and aids. xiii–xiv, 1990.

Robert P. Jacobs, Laure Aurelian, Gerald A Cole Cell–mediated immune response to herpes simplex virus: Journal of Immunology, 116, 1520–1525, 1976.

Laure Aurelian, Ivor Royston, Hugh J. Davis Antibody to genital herpes simplex virus: association Journal of National Cancer Institute, 45, 455–463, 1970.

John W. Nelson, Joa Zhu, Cynthia C. Smith, Michael Kul ATP and SH3 binding sites in the protein kinase of the Journal of Biological Chemistry, 271, 17021–27, 1996.

Theodore D. Chung, James P. Wymer, Michael Kulka, Cynt Myristylantion and polylysine–mediated activation of t Virology 179, 168–178, 1990.

C.C. Smith, J.H. Luo, J.C.R. Hunter, J.V. Ordonez and The transmembrane domain of the large subunit of HSV–2 Virology, 200, 598–612, 1994.

Laure Aurelian Herpes simplex virus type 2: unique biological propert Frontiers in Bioscience, 3, 1–15, 1998.

Jian–Hua Luo and Laure Aurelian The transmembrane helical segment but not the invarian Journal of Biological Chemictry, 267, 9645–53, 1992.

Jian–Hua Luo, Cynthia C. Smith, Michael Kulka, Laure A A truncated protein kinase domain of the large subunit Journal Biological Chemistry, 266, 20976–83, 1991.

J.C.R. Hunter, C.C. Smith, Debashish Bose, Michael Kul Intracellular internalization and signaling pathways Virology, 210, 345–360, 1995.

Raxit J. Jariwalla, Laure Aurelian, Paul O.P. TS'O Tumorigenic transformation induced by a specific frag Proceedings National Acadamy Science 77, 2279–83, 1980.

Theodore D. Chung, James P. Wymer, Cynthia C. Smith, Protein kinase activity associated with the large subu Journal of Virology 63, 3389–98, 1989.

Tao Peng, James R.C. Hunter, John W. Nelson The novel protein kinase of the RR1 subunit of herpes Virology, 216, 184–196, 1996.

J. Conner, J. Murray, A. Cross, J.B. Clements, and H.S Intracellular localisation of herpes simplex virus typ Virology, 213, 615–623, 1995.

J. Cooper, J. Conner, J.B. Clements Characterization of the novel protein kinase activity Journal of Virology, 69, 4979–85, 1995.

Ionnis Nikas, Nohn McLauchlan, Andrew J. Davison, Will Structural features of ribonucleotide reductase Proteins structure Function genetics 1,376–384, 1986.

Yoshinobu Hayashi, Tsuyoshi Iwasaka, Cynthia C. Smith Multistep transformation by defined fragments of herpe Proceedings National Acadmy Science 82, 8493–97, 1985.

VACCINE COMPOSITION FOR HERPES SIMPLEX VIRUS AND METHODS OF USING

This application is a divisional application of U.S. application Ser. No. 09/008,388, filed Jan. 16, 1998, now U.S. Pat. No. 6,054,131, which is incorporated herein by reference.

BACKGROUND OF THE INVENTION

Herpes Simplex Virus (HSV) is a well-studied virus. Both distinguishable serotypes of Herpes Simplex Virus (HSV-1 and HSV-2) cause infection and disease ranging from relatively minor fever blisters on lips to severe genital infections, and generalized infections of newborns. HSV-1 and HSV-2 are 50% homologous at the DNA level, and polyclonal antibodies and MAbs to shared epitopes for one are cross-reactive to the other.

HSV-1 and HSV-2 have RR1 proteins (respectively designated ICP6 and ICP10) that contain a unique amino terminal domain. The HSV-2 unique domain codes for a ser/thr-specific PK which has auto- and transphosphorylating activity and has a transmembrane (TM) domain. Sequences which code for the PK domain cause neoplastic transformation and are associated with cervical cancer (HSV-2 oncogene). The unique terminal domain of the HSV-1 RR1 protein (ICP6) also has PK activity but it is different from that of the HSV-2 oncoprotein, both structurally and functionally.

Original studies, using enzymatic assay conditions similar to those employed for ICP10 PK, concluded that ICP6 does not have PK activity, although the unique domain is retained (Chung et al., J. Virol. 63:3389–3398, 1989). This was not unexpected since the sequence of the unique PK domains showed only 38% homology (Nikas et al., Proteins: Structure, function and genetics 1:376–384, 1986). Further studies indicated that ICP6 has PK activity but only under different conditions. There are conflicting results about its ability to transphosphorylate other proteins (see Peng et al., Virology 216:184–196, 1996 for a review of the problem; particularly Table 1). The reason for the different PK activities of the ICP6 and ICP10 proteins is likely to be that the ICP6 PK ATP binding sites are located distantly from the rest of the catalytic motifs (Cooper et al., J. Virol 69:4979–4985, 1995). ICP6 also does not have a functional TM domain and it does not localize to the cell surface (Conner et al., Virology 213:615, 1995). The PK activity of the native ICP6 is very weak even under ideal conditions, such that its $K_m$ is 10-fold higher than that of ICP10 PK (Peng et al., Virology 216:184, 1996; Lee and Aurelian, in preparation).

The transforming activity of ICP6 is located within a genome fragment that is distant from that at which the HSV2 oncogene is located. Transformation in this system is morphologic (focus forming ability).

It has previously been shown that DNA sequences which encode for the amino-terminal one-third of ICP10 (amino acids 1–417) have oncogenic potential. Cells transfected with these DNA sequences evidence anchorage independent growth and cause tumors in animals. Transformation is seen in both rodent and human cells (Jariwalla et al., PNAS 77:2279–2283, 1980; Hayashi et al., PNAS 82:8493–8497, 1985; Smith et al., Virology 200:598–612, 1994; Hunter et al., Virology 210:345–360, 1995).

There are three functional domains within ICP10 amino acids 1–41 1: (i) an intracellular domain, at amino acids 106–411, which encompasses the PK catalytic domain with eight conserved catalytic motifs (amino acids 106–411), (ii) a TM, at amino acids 88–105, and (iii) an extracellular domain at amino acids 1–88 (Chung, et al., J. Virol. 63:3389–3395, 1989; Virology 179:168–178, 1990). The minimal size required for PK activity is amino acids 1–283 ($pp29^{Ia1}$) (Luo et al., J. Biol. Chem. 266: 20976–20983, 1991). However, the PK activity of $pp29^{Ia1}$ has some properties different from the authentic ICP10 PK, presumably because it lacks part of the PK catalytic domain VI (Luo et al., J. Biol. Chem. 266: 20976–20983, 1991). The TM domain is also required (but insufficient) for PK activity (Luo and Aurelian, J. Biol. Chem. 267:9645–9653, 1992). Therefore, it can be concluded that the PK activity is localized within amino acids 88411 with an essential core at amino acids 88–283.

The unique HpaI site within the ICP10 coding region represents the 3' end of the transforming region (Jariwalla et al., Proc. Nat. Acad. Sci. 77:2279–2283, 1980) and cuts the gene after the codon for amino acid residue 417. It is not known whether $pp29^{Ia1}$ has transforming activity. However, PK activity is required for neoplastic potential. PK negative mutants do not transform cells. This includes a mutant deleted in the TM domain and site directed mutants in the ATP binding sites ($Lys^{176}$ and/or $Lys^{259}$) or the ion-binding site ($Glu^{209}$) (Smith et al., Virology 200:598–612, 1994; Aurelian, L. Frontiers in Biology, in press). Because a PK⁻ mutant deleted only in the TM domain does not have transforming activity (Smith et al., Virology 200:598–612, 1994), DNA sequences that code for ICP10 amino acids 106–411, but lack PK activity, are not intrinsically neoplastic. This demonstrates that: (i) the HSV-2 oncoprotein is located within ICP10 amino acids 1–411, and (ii) neoplastic potential requires a functional PK activity.

The function of ICP10 PK in virus growth/pathogenesis is unknown.

The HSV-2 ICP10 protein has intrinsic PK activity. This was shown by demonstrating that ICP10 PK activity is lost through site-directed mutagenesis. The oncogene also has SH3 -binding sites at positions 140, 149 and 396, which are required for interaction with signaling proteins. This interaction is required for transforming activity. Site directed mutagenesis was used to identify amino acids required for kinase activity and interaction with signaling proteins. Mutation of $Lys^{176}$ or $Lys^{259}$ reduced PK activity (5–8 fold) and binding of the $^{14}$C-labeled ATP analog p-fluorosulfonylbenzoyl 5'-adenosine (FSBA), but did not abrogate them. Enzymatic activity and FSBA binding were abrogated by mutation of both Lys residues, suggesting that either one can bind ATP. Mutation of $Glu^{209}$ (PK catalytic motif III) virtually abrogated kinase activity in the presence of $Mg^{2+}$ or $Mn^{2+}$ ions, suggesting that $Glu^{209}$ functions in ion-dependent PK activity.

ICP10PK functions as a growth factor receptor involved in signaling and it binds the adaptor protein $Grb_2$ in vitro. The SH3-binding sites within the ICP10 PK domain (at positions 140, 149 and 396) are required for interaction with signaling proteins and, thereby transformation (Nelson et al., J. Biol. Chem. 271:17021–17027, 1996). Mutation of the ICP10 proline-rich motifs at position 396 and 149 reduced $Grb_2$ binding 20- and 2-fold respectively. Binding was abrogated by mutation of both motifs. $Grb_2$ binding to wild type ICP10 was competed by a peptide for the Grb2 C-terminal SH3 motif indicating that it involves the $Grb_2$ C-terminal SH3 (Nelson et al., J. Biol. Chem. 271:17021–17027, 1996).

The ICP10 PK catalytic domain also contains amino acids at position 106–178 that are responsible for binding a down-regulator of PK activity (ras-GAP). Deletion of amino acids 106–178 reduces, but does not abrogate, PK activity (Luo and Aurelian, J. Biol. Chem. 267:9645–9653, 1992). However, it abrogates ras-GAP binding, thereby increasing transforming potential (Nelson et al., manuscript in preparation).

The construction of the ICP10 PK virus is described by Peng et al. (Virology 216, 184–196, 1996). Briefly, the wild type sequences in a plasmid (TP101) that contains the HSV-2 BamHI E and T fragments were replaced with the 1.8kb SalI/BglII fragment from pJHL9. pJHL9 is a plasmid containing the ICP10 mutant deleted in the PK catalytic domain (Luo and Aurelian, J. Biol. Chem. 267:9645–9653, 1992). The resulting plasmid, TP9, contains sequences which code for ICP10 deleted in the PK catalytic domain flanked by 4 and 2.8 kb of HSV-2 DNA sequences at the 5' and 3' ends, respectively. The 10 kb HindIII/EcoRI fragment from TP9 was introduced by marker transfer into a virus (ICP10ΔRR) in which the RR domain of ICP10 had been replaced with the LacZ gene. The resulting recombinant virus, designated ICP10ΔPK, was obtained by selecting white plaques on a background of blue plaques after staining with X-gal. A few white plaques were picked and purified. Two were grown in Vero cells with 10% serum (exponentially growing) into individual stocks respectively designated RF and CS.

There are several known HSV vaccines in the prior art. U.S. Pat. Nos. 4,347,127; 4,452,734; 5,219,567; and 5,171,568 each teach subunit vaccines which provide some protection against HSV-2 infection. These vaccines are inferior to one in which a live, attenuated virus is used. The immunity induced by a subunit vaccine is restricted to the particular protein represented by the subunit, which may not have sufficient protective potential. Additionally it is non-replicating and there is, therefore, no amplification of the protein which would further reduce immunogenicity. These problems occur in any subunit vaccine regardless of whether the method of preparation is via a recombinant protein or the purification of an antigen from the virus.

A cross recombinant vaccine, such as disclosed in U.S. Pat. No. 4,554,159, does not suffer from the problems of the subunit vaccines, but contains the oncogene present in HSV-2. Unless care is taken to define and delete the oncogene, the cross recombinant vaccine would induce cancer in the vaccinee.

The cross recombinant of '159 is temperature sensitive. Avirulence may be obtained by selecting temperature resistance, but the temperature of the mouse is 39° C. while that of humans is 37° C. This temperature sensitivity could well render such a cross problematic in a vaccine. A superior method of selection of avirulence is by the removal of genes coding for virulence without respect to the temperature at which the virus replicates. Also, the use of prototypical crosses would preclude the use of mutants with deleted or inserted genes.

Due to the many type-common epitopes on HSV-1 and HSV-2, the antibodies in human serum are cross-reactive (Aurelian, et al., J. Natl. Cancer Inst. 45:455464, 1970.) It has also been previously shown that cell-mediated immunity cross-reacts (Jacobs et al., J. Immunol. 116:1520–1525, 1976).

A live vaccine is superior to a dead vaccine because the live vaccine induces herd immunity and it also induces different types of immunity, such as mucosal, cell mediated and humoral immunity. A higher level of immunity is normally obtained because the virus titers are increased through replication within the vaccinee. Finally a live vaccine is of longer duration, thus obviating boosters and lowering initial dosage. However, an absolute necessity for a live herpes vaccine is the removal of the gene responsible for causing transformation, as in the present invention. Known vaccines are not virus type-specific. All known vaccines for HSV-1 or HSV-2 are cross-reactive and provide immunity to the other virus type. Most developed vaccines (viz. those in neurovirulence genes) are in HSV-1. However, HSV-1 is not as desirable a vaccine candidate against herpes, because the major clinical problem is the sexually transmitted HSV-2, which is also associated with cancer induction. Recent studies indicate that the age-adjusted prevalence of HSV-2 in the US is now 20.8%, an increase of approximately 30% over the past 13 years (Fleming et al., New Engl. J. Med. 337:1105–1111, 1997). The increasing rate of HSV-2 acquisition among young adults increases the likelihood that infants will be exposed to HSV-2 at delivery, resulting in an infection that, despite antiviral therapy, is still life-threatening (Whitley, et al., New Engl. J. Med. 327:782–799, 1992 [Erratum, N. Engl. J. Med. 328:671, 1993]). A new concern about HSV-2 infection is that it may facilitate the spread of HIV and increase the severity of the disease (Aurelian, L. Editor. Herpes viruses, the Immune System and AIDS. Kluwer Academic Publishers, Boston, Mass. 1990). Because HSV-1 has only a 50% homology to HSV-2, this may lower the response rate against the heterologous strain in the vaccinated population.

Another absolute requirement for a live vaccine is the absence of lesions upon immunization. A desirable trait in the live vaccine would be its ability to cause a reduction in the frequency of recurrent lesions in a person already infected. There is a substantial population already infected with HSV who may have intercourse with uninfected individuals who would benefit from such a vaccine.

The present invention solves all the problems recited above providing a whole live attenuated HSV-2 in which the HSV-2 has a deletion of the oncogene, and is formulated in a vaccine composition. The present invention provides a method of immunizing a subject against HSV-1 or HSV-2 with said vaccine composition, providing a superior method of conferring immunity upon the subject.

SUMMARY OF THE INVENTION

It is an object of the present invention to provide a vaccine composition which when administered to an animal, including a human, provides protection from challenge with HSV-2 or HSV-1 infection.

It is a further object of the invention to provide a vaccine composition comprising whole, live, attenuated HSV-2 wherein the oncogene or any portion thereof that causes transformation and does not attenuate the virus has been deleted.

It is a further object of the invention to provide a method of immunizing a subject against HSV-2 or HSV-l comprising administering a novel vaccine composition.

It is even a further object of the present invention to reduce or prevent clinical symptoms associated with HSV-2 or HSV-I infections comprising administering a novel vaccine composition.

It is yet a further object of the present invention to reduce recurrent disease associated with HSV-2 or HSV-1 in previously infected subjects comprising administering a novel vaccine composition.

BRIEF DESCRIPTION OF THE DRAWINGS

FIG. 1A. Schematic representation of ICPI0ΔPK DNA. Oligoprobe AU26 should recognize the 7.6kb BamHI E fragment from HSV-2 or HSV-2(R) DNA and a 2.2kb BamHI fragment from ICP10ΔPK DNA.

B. Southern blot hybridization of BamHI digested ICP10ΔPK (lane 1), HSV-2 (lane 2), or HSV-2 (R) (lane 3) DNA with the digoxigenin-labeled AU26 oligoprobe. Size markers are shown in the right margin. Similar results were obtained for ICP10ΔPK stocks RF and CS.

Figure 2:
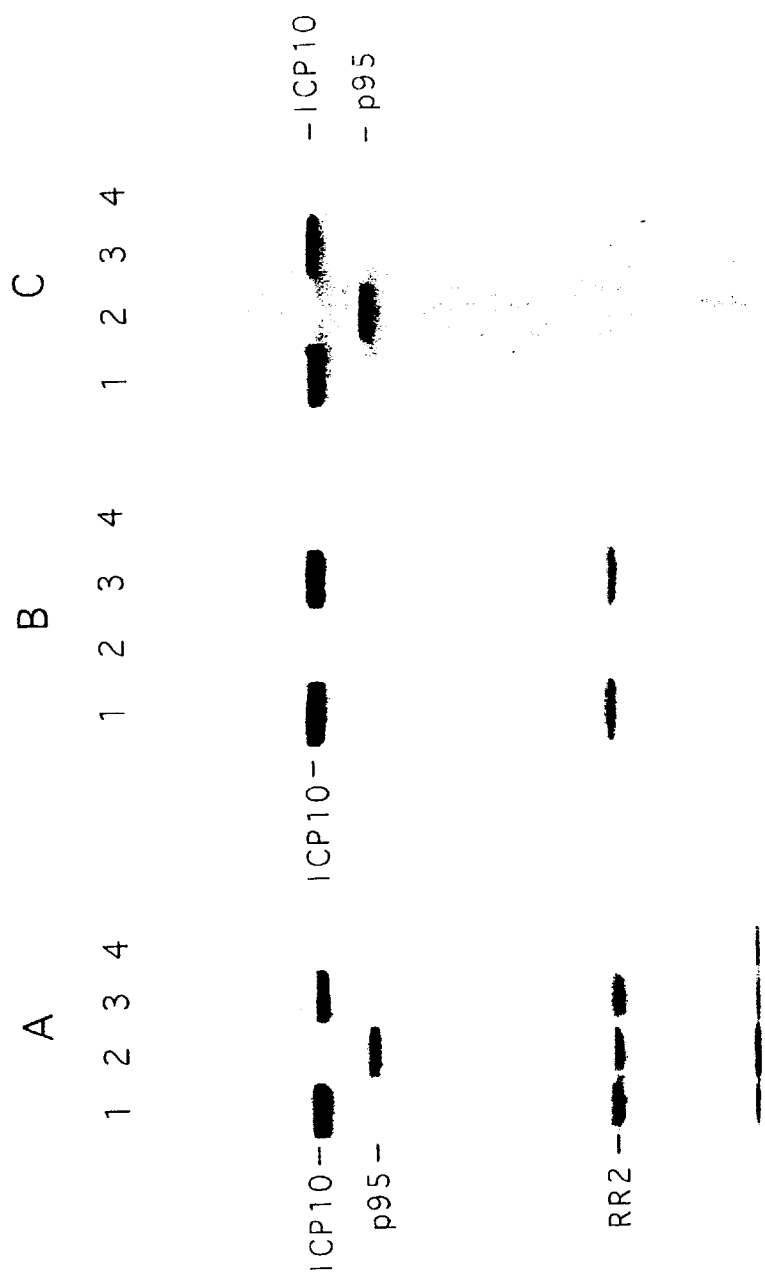

FIG. 2 Expression and PK activity of the p95 protein from ICP10ΔPK infected cells.

A. Vero cells were infected with HSV-2 (lanes 1,4), ICP10ΔPK (lane 2), or HSV-2(R) (lane 3), labeled with [$^{35}$S]-methionine from 6–16 hrs p.i. and extracts were immunoprecipitated with anti LA-1 antibody which is specific for ICP10 (lanes 1–3) or preimmune serum (lane 4).

B. Immunocomplex PK assay with anti LA-I antibody (lanes 1–3) or preimmune serum (lane 4) of extracts from Vero cells infected for 16 hrs with HSV-2 (lane 1,4), ICP10ΔPK (lane 2) or HSV-2(R) (lane 3).

C. The immunoprecipitates in Panel B were immunoblotted with anti LA-1 antibody. Similar results were obtained for ICP10ΔPK stocks RF and CS.

Figure 3:
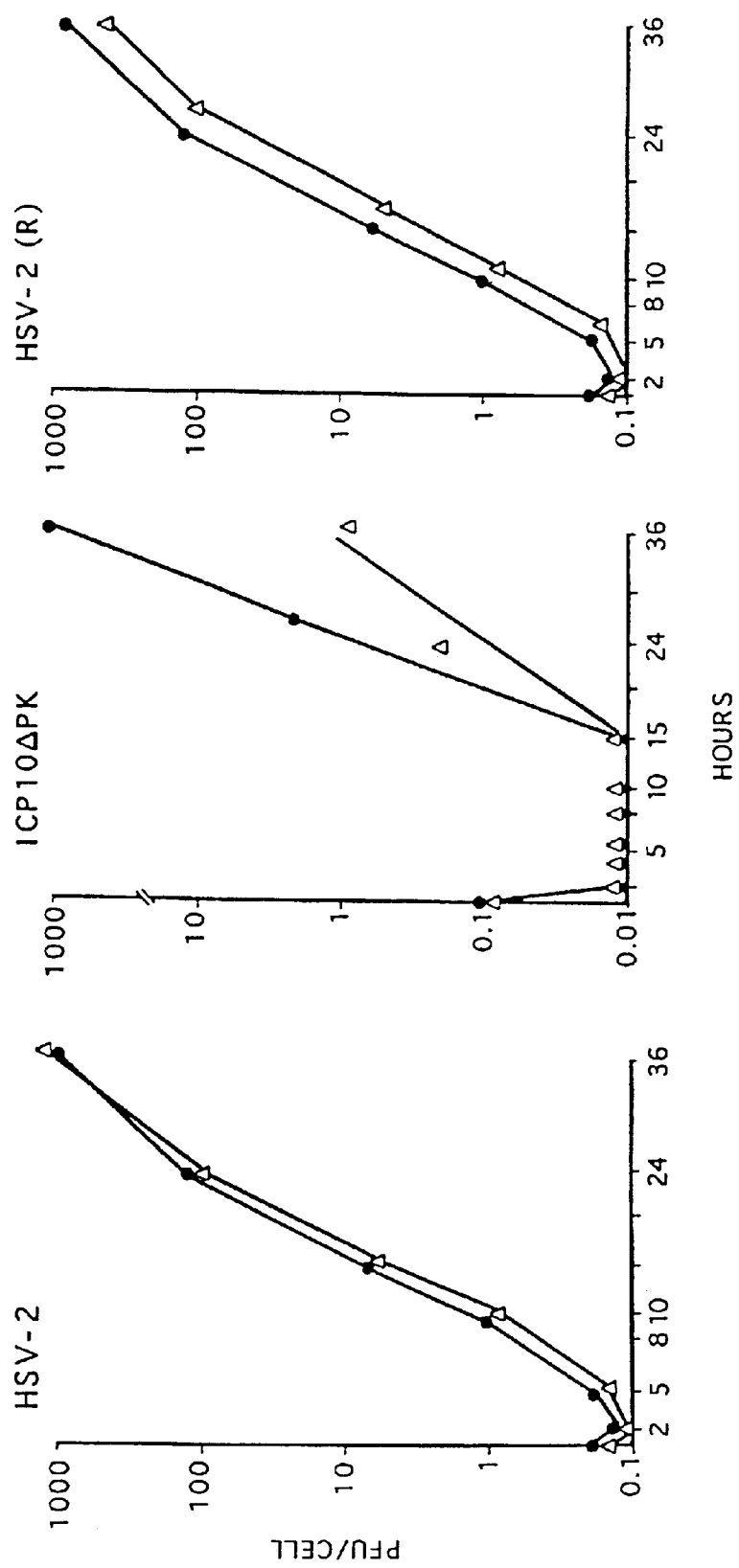

FIG. 3 Virus growth under exponential and growth restricted conditions. Vero cells grown in 10% serum (●) or 0.5% serum (Δ) were infected with HSV-2, ICP10ΔPK, or HSV-2(R) at an moi of 2. Virus titers were assayed at 2 to 36 hrs. p.i. Results are expressed as PFU/cell (burst size).

Figure 4:
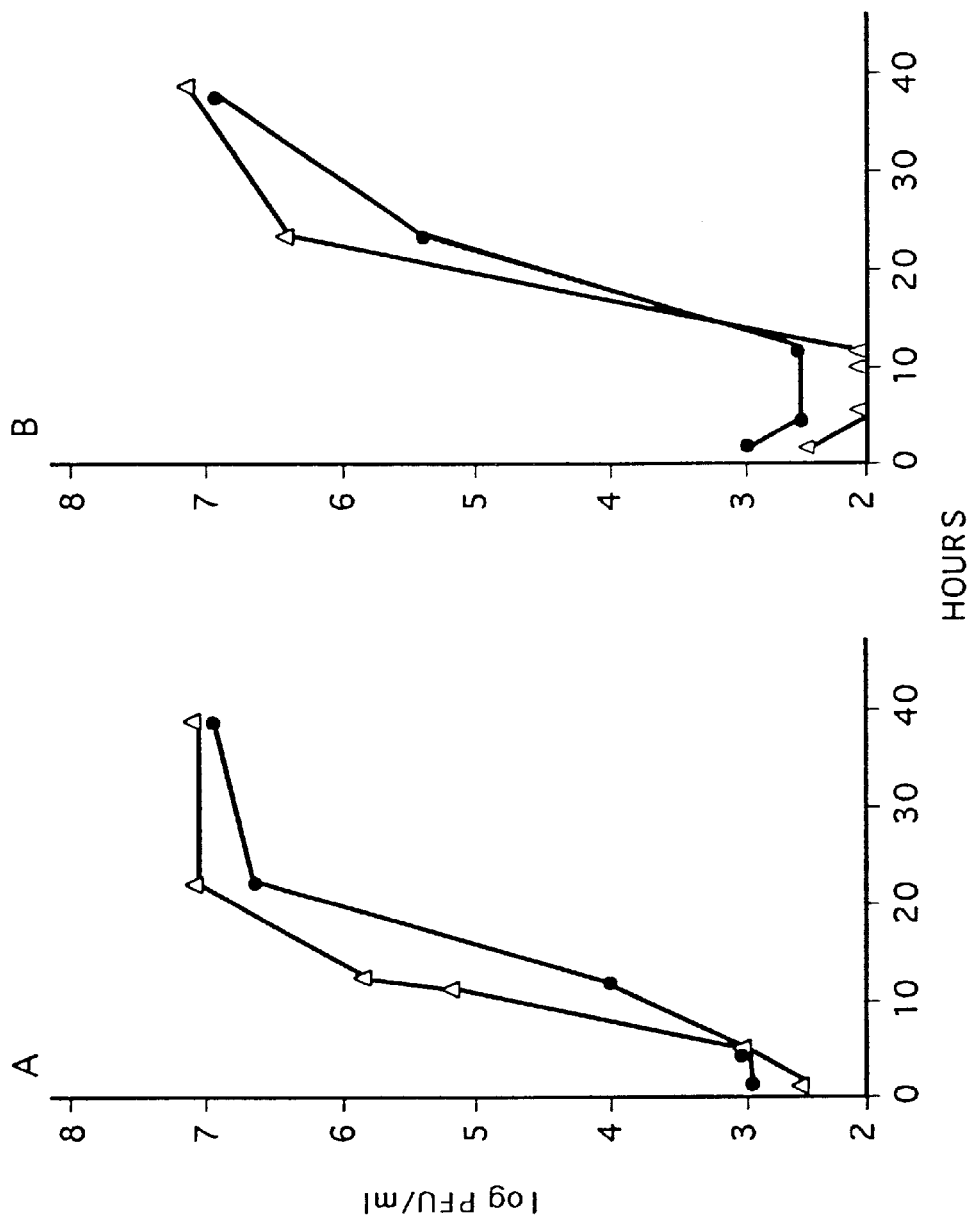

FIG. 4 Extracellular and intracellular virus titers in Vero cells infected at a high moi. Exponential Vero cells were infected with HSV-2 (A) or ICP10ΔPK (B) at an moi of 200 and intracellular (Δ) and extracellular (●) virus titers were determined at 2 to 36 hrs. p.i.

Figure 5:
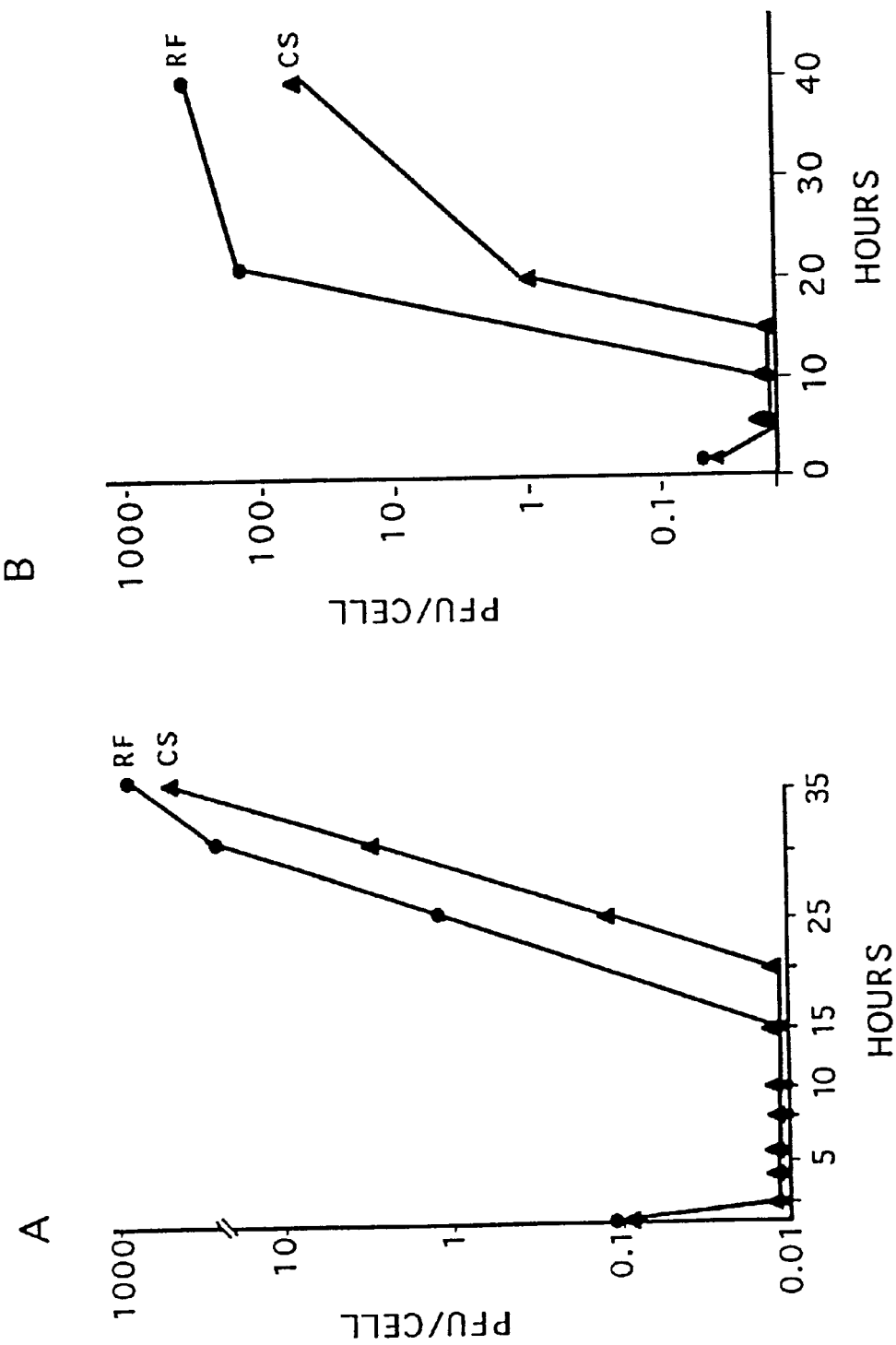

FIG. 5 Virus growth in dividing cells infected with the two ICP10ΔPK stocks. Vero cells were grown in medium with 10% serum and infected with ICP10ΔPK (RF) (●) or ICP10ΔPK (CS) (Δ). Infection was at moi of 2 (panel A) or 200 (panel B).

Virus titers were determined at 2–35 hrs. p.i and results are expressed as PFU/cell (burst size).

Figure 6:
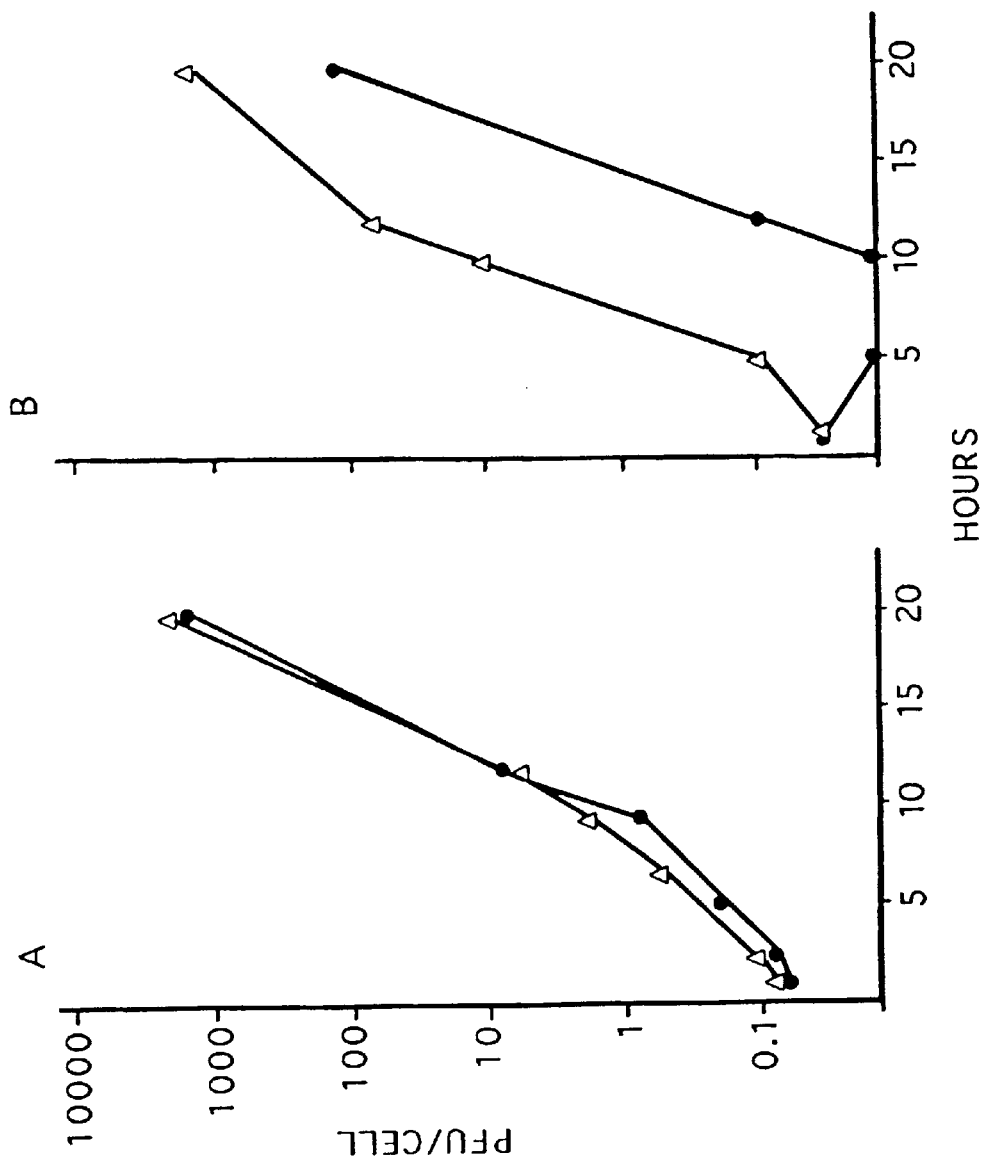

FIG. 6 ICP10ΔPK virus growth in cells that constitutively express ICP10. JHLa1 cells, that constitutively express ICP10 (Panel A) or 293 cells, that were used to establish the JHLa1 line (Panel B), were infected with HSV-2 (Δ) or ICP10ΔPK stock RF (●) at an moi of 200. Virus titers were assayed at 2 to 20 hrs p.i. Results are expressed as PFU/cell (burst size). Similar results were obtained for ICP10ΔPK sock C in JHLa1 cells.

Figure 7:
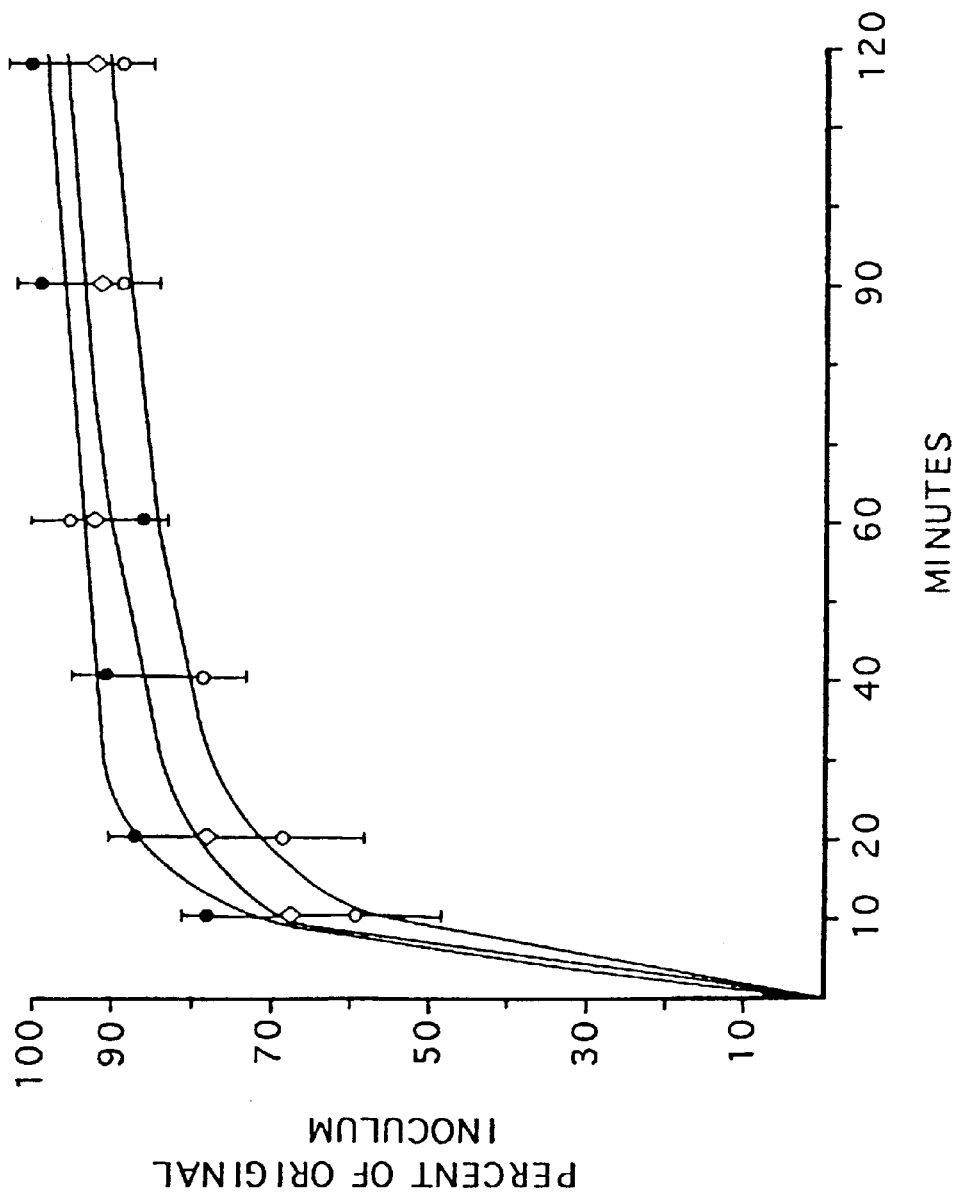

FIG. 7 Adsorption/penetration kinetics of ICP10ΔPK. Vero cells were exposed to 200 pfu of HSV-2 (●) ICP10ΔPK (o) or HSV-2) (R)(◊) for 0, 10, 30, 60, 90, 120 min., overlaid with MEM 10% serum and 0.3% IgG, reincubated at 37° C. for 48 hrs and scored for plaque formation. Data are presented as the % of the original inoculum. Similar results were obtained for ICP10ΔPK stocks RF and CS.

Figure 8:
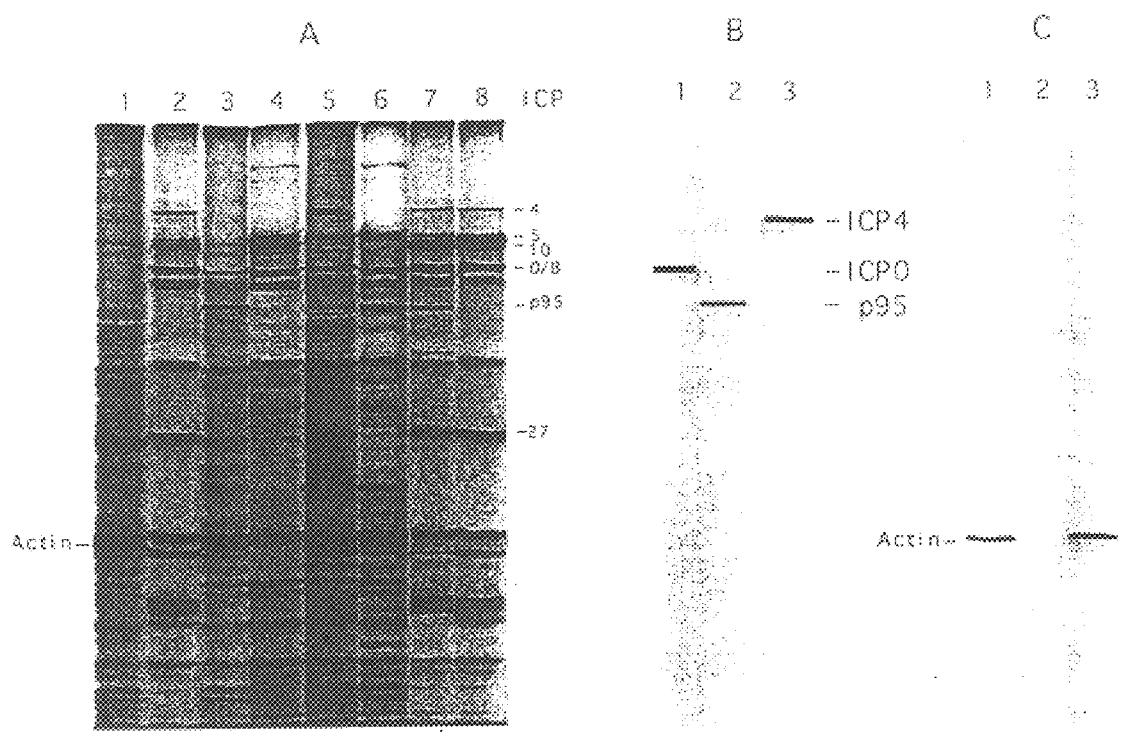

FIG. 8 Protein profiles of HSV-2 and ICP10ΔPK infected cells.

A. Vero cells (lanes 1–6, 8) were mock infected (lane 1) or infected with HSV-2 (lanes 2, 4), ICP10ΔPK (RF) (lanes 3, 5, 6,) or HSV-2 (R) (lane 8) and labeled with [$^{35}$S]-methionine from 2–3 hrs p.i., (lanes 1–3, 8), 7–8 hrs p.i. (lanes 4, 5), or 11–12 hrs p.i. (lane 6). The protein profile in JHLa1 cells (constitutively express ICP10) infected with ICP10ΔPK, and labeled with [$^{35}$S]-methionine from 2–3 hrs p.i. served as control (lane 7). Proteins from cell extracts were resolved by PAGE on 8.5% SDS acrylamide gels.

B. Extracts of cells infected with ICP10ΔPK (RF) for 3 hrs (lanes 1,2) or 8 hrs p.i. (lane 3) were immunoblotted with ICP0MAb (lane 1), LA-1 antibody to ICP10 (lane 2) or ICP4 MAb (lane 3).

C. Extracts of Vero cells mock infected (lane 1), infected with HSV-2 for 3 hrs (lane 2) or ICP10ΔPK for 12 hrs. were immunoblotted with antibody to actin.

Figure 9:
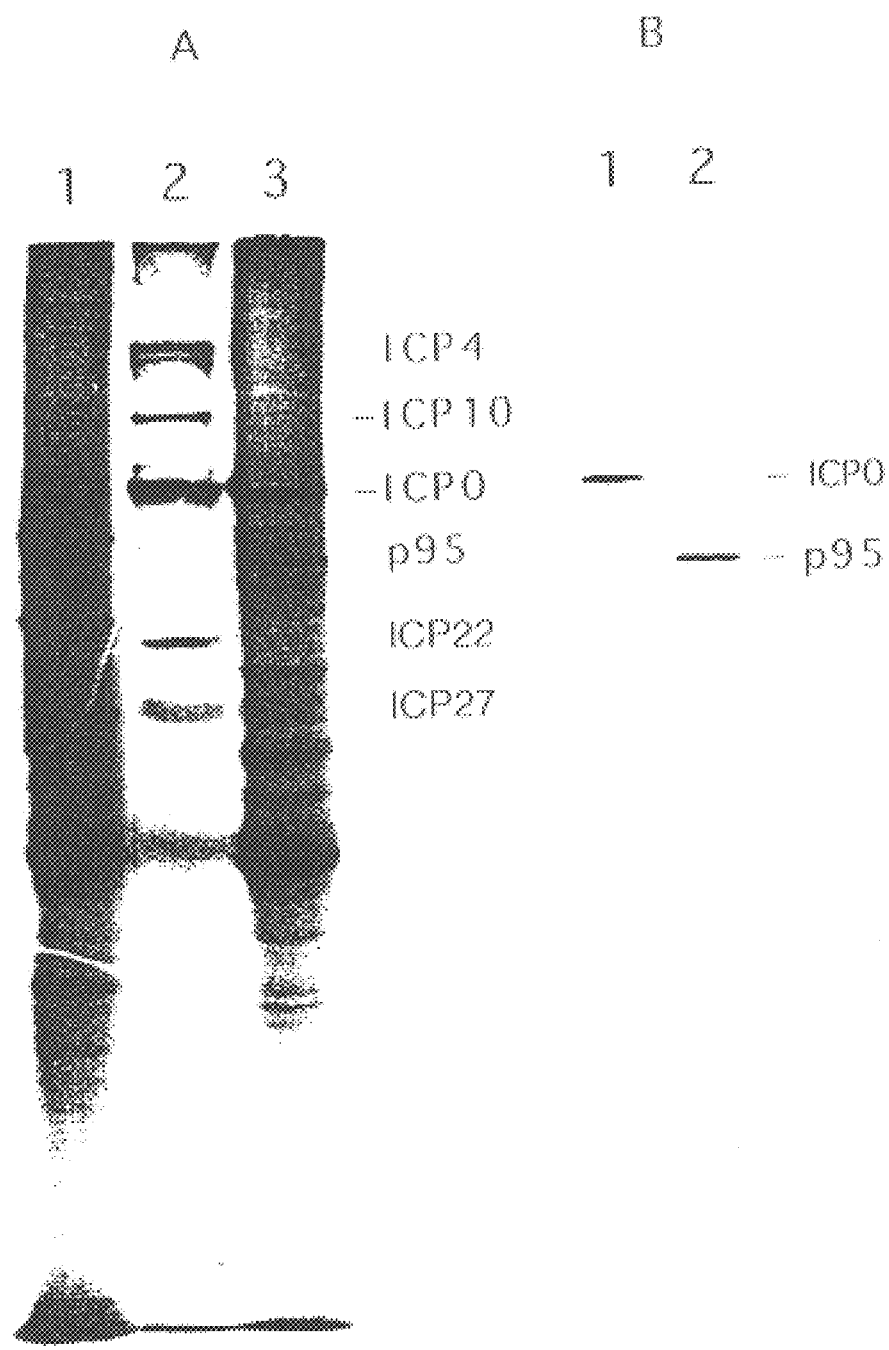

FIG. 9 IE protein synthesis in HSV-2 and ICP10ΔPK infected cells.

A. Vero cells were mock infected (lane 1) or infected with HSV-2 (lane 2) or ICP10ΔPK (RF) (lane 3) in the presence of 50 μg/ml cycloheximide (6 hrs) and labeled with [$^{35}$S]-methionine for 3 hrs in medium containing 10 μg/ml actinomycin D. Proteins were resolved by PAGE on 8.5% SDS acrylamide gels.

B. Immunoblotting of extracts in lanes 2,3 in panel A with ICP0 MAb (lane 1) and anti-LA-1 antibody to ICP10 (lane 2).

Figure 10:
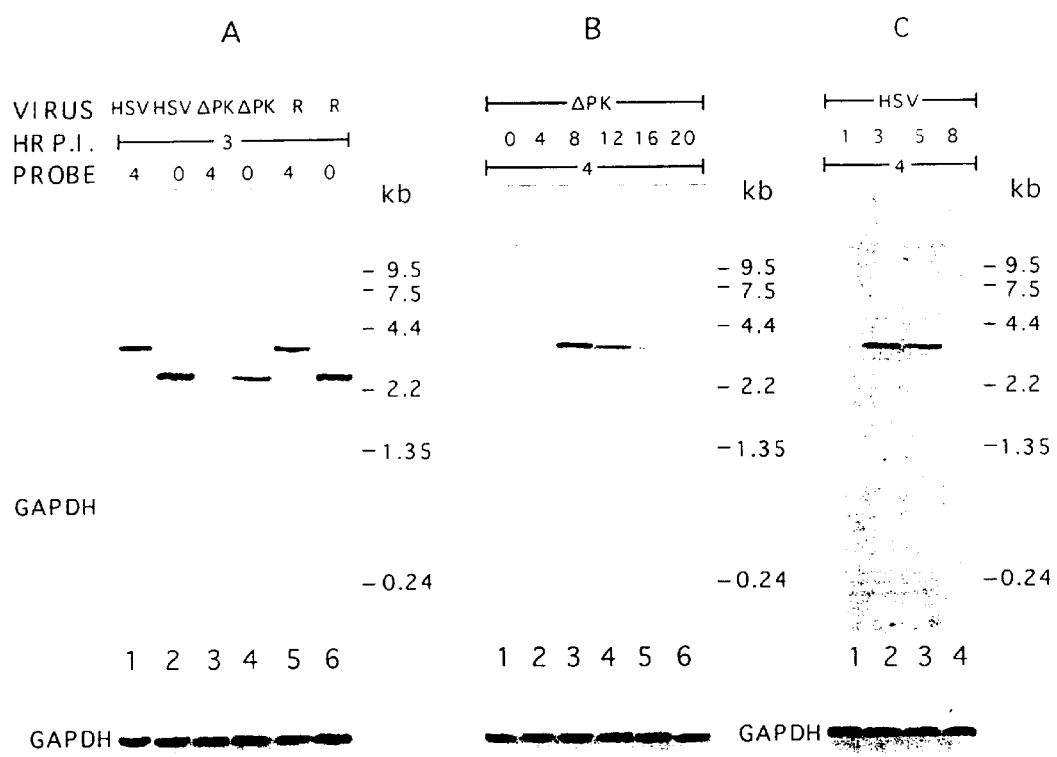

FIG. 10 ICP4 and ICP0 mRNA synthesis in cells infected with ICP10ΔPK. RNA was extracted from Vero cells infected with HSV-2 (HSV) or ICP10ΔPK (ΔPK) or HSV-2 (R)(R) for 3 hrs (panel A) 0–20 hrs (panel B) or 1–8 hrs (panel C) as listed.

It was hybridized with [$^{32}$P]-labeled ICP4 (4) or ICP0 (0) DNA probes or GAPDH oligonucleotide (bottom panel). Molecular weight markers are indicated in the margins.

Figure 11:
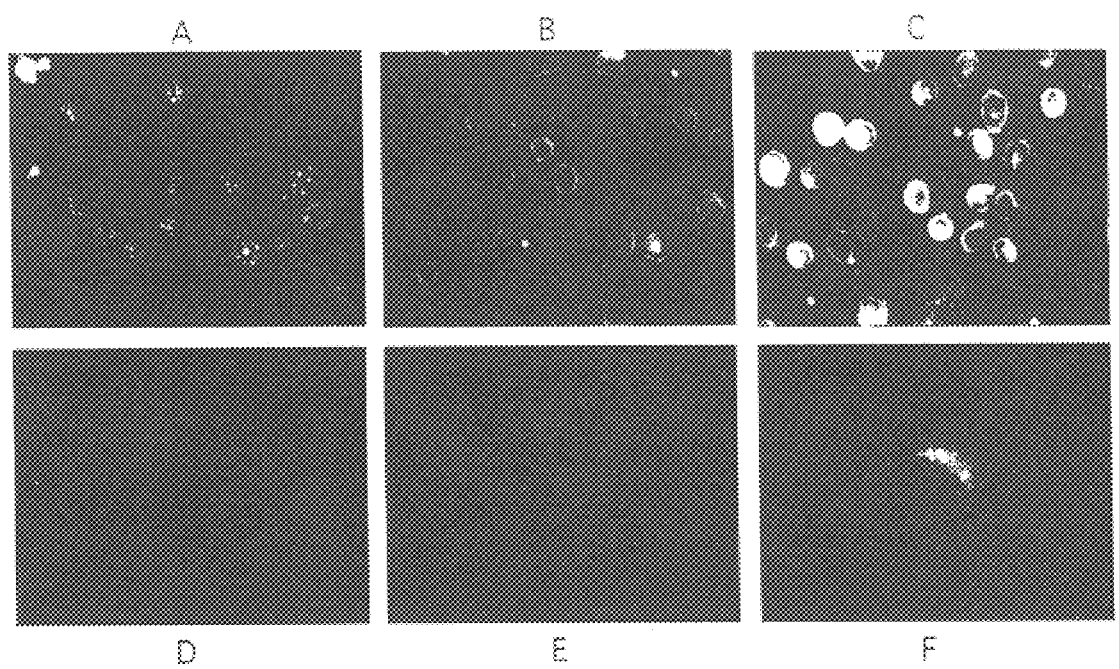

FIG. 11 Indirect immunofluorescent staining of Vero cells infected with HSV-2 (Panels A,B,C) or ICP10ΔPK (RF) (Panels D,E,F) for 3 hrs (Panels A,D), 6hrs (Panels B, E) or 9 hr (Panels C,F) and stained with MAb 30 (Panels A–C ) or anti LA-I antibody to ICP10 (Panels D–F).

Figure 12:
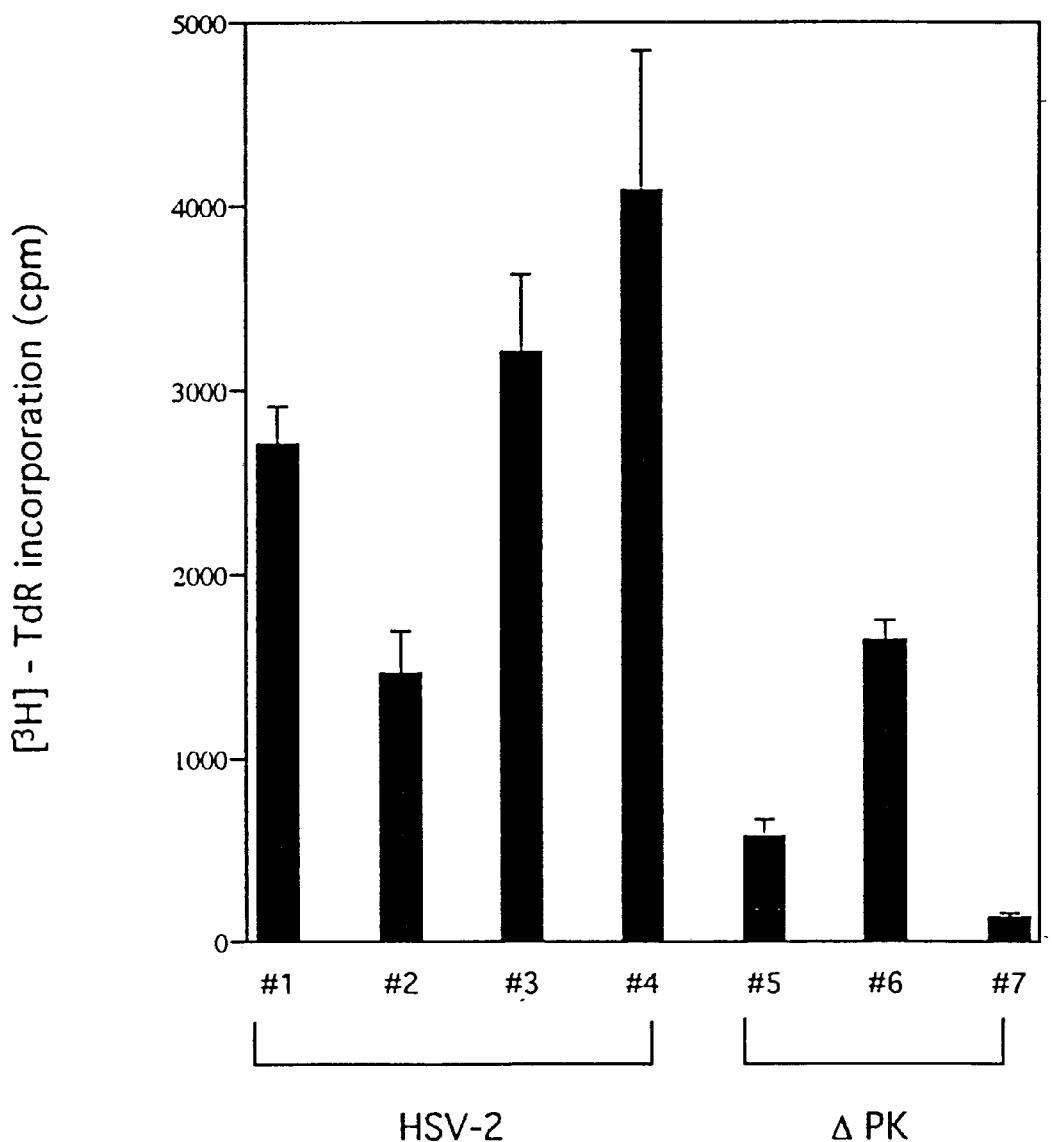

FIG. 12 HSV-specific lymphoproliferative responses of spleen cells from mice immunized with ICP10ΔPK (stock RF). Mice were given sc injection with 1×10$^6$ pfu of HSV-2 or ICP10ΔPK (ΔPK). Spleens were collected on day 24 p.i. and assayed for [$^3$H]-TdR incorporation (cpm). Results are expressed as cpm for HSV-stimulated cultures—cpm for cultures stimulated with mock antigen.

Figure 13:
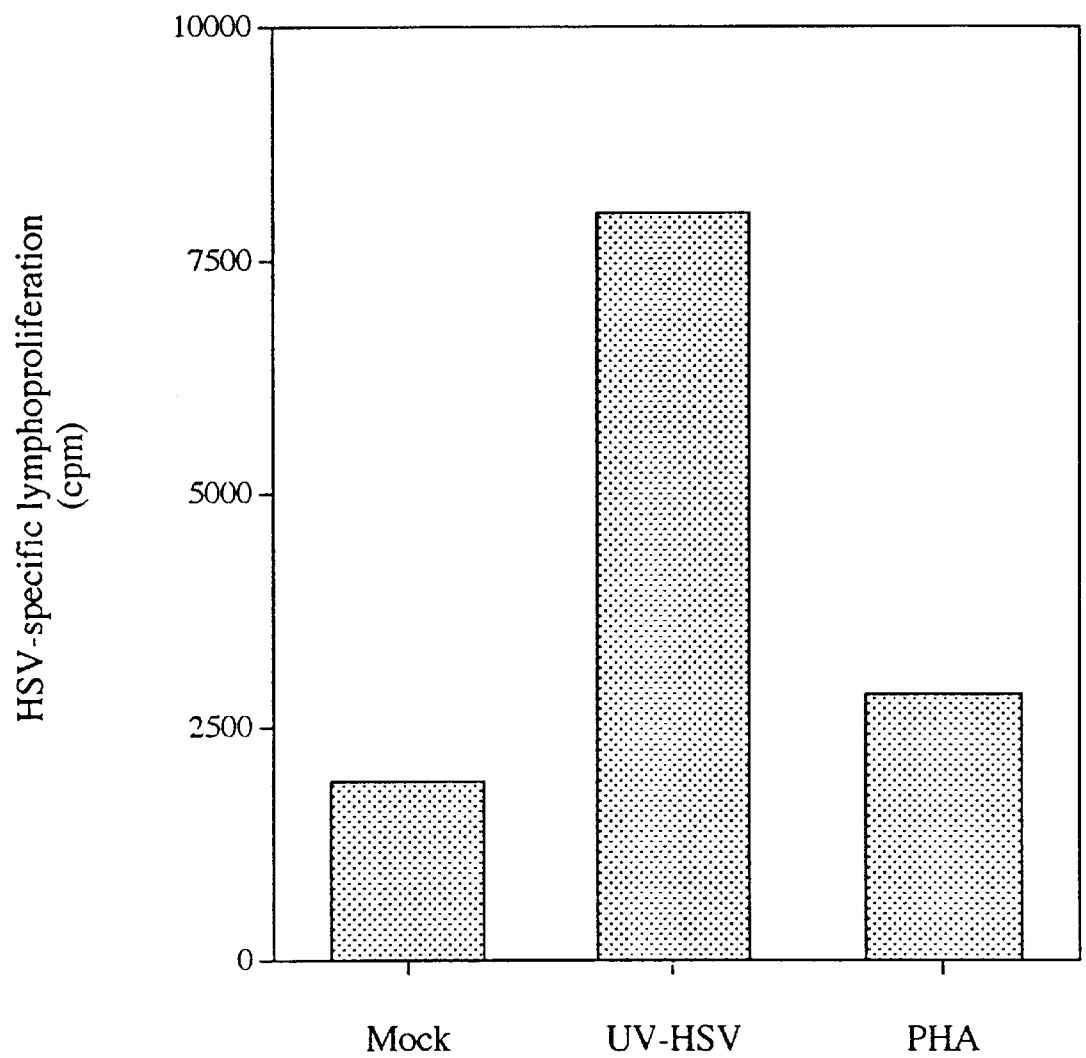

FIG. 13 HSV-specific lymphoproliferative responses of spleen cells from mice immunized ICP10ΔPK (stock CS). Mice were given three sc injections with 1×10$^7$ pfu of ICP10ΔPK (ΔPK). Spleens were collected on day 14 after the last injection and assayed for [$^3$H]-TdR incorporation (cpm) after culture with HSV-2 or mock antigens or the mitogen PHA.

DETAILED DESCRIPTION OF THE INVENTION

In the present invention, live whole HSV-2 has been mutated and attenuated to prevent neoplastic transformation. The mutated HSV-2 can be formulated with immune stimulants or adjuvants and used to immunize a subject against HSV-1 or HSV-2. The protein kinase domain of the large subunit of ribonucleotide reductase (ICP10) has previously been shown to have oncogenic properties. Deletion of the PK domain is shown in the present invention to have deleterious effects on the ability of HSV-2 to infect cells. The present invention demonstrates for the first time that live HSV-2 lacking the ICP10PK domain, and hence the oncogene, provides immunogenic protection against challenge with live wild type HSV-2. Therefore, a novel vaccine composition has been discovered and a novel method of immunizing a subject against HSV-2 or HSV-1.

HSV-1 and HSV-2 viruses are very similar. The DNA is 50% homologous. Virtually all viral proteins have both type-specific and type-common epitopes. For all but 2 proteins (i.e., for 82 proteins), the type-common epitopes are predominant. The exception is the HSV-2 gG2 (Ashley et al., J. Clin. Invest. 90:511, 1992) and the HSV-2 oncoprotein which elicit predominantly type-specific antibodies. In the present invention, the HSV-2 oncogene was deleted from ICP10ΔPK. Therefore we only have one protein that can induce type specific immunity. The remaining 83 proteins will induce type common immunity. This incudes both antibody and cell mediated immunity.

Previously, live whole HSV-2 could not be explored as a vaccine option for HSV since the oncogene had potential neoplastic implications for the patient. The present invention demonstrates that by removing the oncogene, a protein kinase, from the HSV-2 genome, not only are the neoplastic properties removed, but the virus is attenuated and provides full protection against challenge for an extended period of time.

The particular HSV-2 strain which contains the deleted oncogene is not critical to the present invention. Examples of such strains include HSV-2(G), HSV-2(333), HSV-2 (186), HSV-2(S-1), although any strain is acceptable. These strains are well known and readily available.

The construction of the mutant virus is accomplished by well known techniques. The location of the oncogene (PK) is well-known (DNA Tumor Viruses Oncogenic Mechanisms, Ed. C. Barbanti-Brodano, et al., Plenum Press, NY, 1995, chapter 14 by L. Aurelian, Transformation and Mutagenic Effects Induced by Herpes Simplex Virus Types 1 and 2, p253–280). The oncogene is located in the ICP10 section of the HSV-2 genome. It has previously been shown that the PK activity and oncogenic activity are located within the gene sequence encoding ICP10 amino acids 88–411. Briefly, the wild type sequences in a plasmid (TP101) that contains the HSV-2 BamHI E and T fragments were replaced with the 1.8kb SalI/BglII fragment from pJHL9 [ICP10 mutant deleted in the PK domain, Luo and Aurelian, J. Biol. Chem. 267:9645–9653, 1992)]. The resulting plasmid, TP9, contains sequences which code for ICP10 deleted in the PK catalytic domain flanked by 4 and 2.8 kb of HSV-2 DNA sequences at the 5' and 3' ends, respectively. The 10 kb HindIII/EcoRI fragment from TP9 was introduced by marker transfer into a virus (ICP10ΔRR) in which the RR domain of ICP10 had been replaced with the LacZ gene. The resulting recombinant virus, designated ICP10ΔPK, was obtained by selecting white plaques on a background of blue plaques after staining with X-gal. A few white plaques were picked and purified. Two were grown in Vero cells with 10% serum (exponentially growing) into independent stocks, respectively designated RF and CS.

Southern blot hybridization was used to confirm that the DNA in the ICP10ΔPK virus is deleted in the ICP10 PK coding region. DNA from HSV-2 and ICP10ΔPK was digested with BamHI, separated on 1% agarose gels and transferred to nylon membranes. It was hybridized with the AU26 (CCCCTTCATCATGTTTAAGGA) probe which recognizes a sequence within the ICP10 RR coding region. The hybridizing band seen for ICP10ΔPK DNA was 2.2 kb as compared to 7.6 kb for wild type HSV-2. Similar results were obtained for stocks RF and CS.

ICP10ΔPK virus can be differentiated from wild type HSV-2 by DNA analysis and immunoprecipitation/immunoblotting with antibody to epitopes located at ICP10 amino acids retained by the deleted protein.

ICP10ΔPK was precipitated/immunoblotted with anti-LA-1 antibody (recognizes ICP10 amino acids 13–26) (Aurelian, et al., Cancer Cells 7:187–191, 1989) and the proteins were resolved by SDS-PAGE. A 95kDa protein was recognized by the antibody in cells infected with ICPlOΔPK virus, as compared to the 140 kDa protein from cells infected with the wild type virus. Similar results were obtained for stocks RF and CS.

The oncogene or any portion thereof may be deleted. By the expression "or any portion thereof" we mean any portion of the oncogene which once deleted results in attenuation of the virus and prevents neoplastic transformation of the cells. Determining if PK activity is absent requires expression of the viral gene and subjecting the result to standard PK assays (Chung et al., J. Virol., 63:3389–3398, 1989). There is abundant guidance in the prior art as to the section of the ICP10 gene which is required for PK activity. Determining viral attenuation requires testing in animals to determine absence of lesion formation. The techniques for accomplishing this are standard and well-known in the art.

The resultant mutant virus, ICP10ΔPK was used in infection experiments and compared to infections with wild-type HSV-2 and restored HSV-2(R) virus. The cells used in infection are not critical to the present invention. Any human or animal cell line which can be infected with wild type HSV-2 may be used in the present invention. Examples of such cell lines include Vero cells, HeLa cells, 293 cells, or MRC5 cells (all available from American Type Culture Collection). ICP10ΔPK can also be grown in cells that constitutively express ICP IO, for example JHLa1. It is titrated by plaque assay on Vero cells with MEM-10% FCS and 0.3% human IgG. The growth properties of the RF and CS virus stocks were independently determined.

The infection experiments were also conducted in animals. Mice were chosen since mice represent the standard animal model for HSV-2 (Wachsman et al., Vaccine 10:447–454, 1992). The mouse footpad model was chosen to examine the pathogenicity of the ICP10ΔPK virus in vivo. The RF and CS virus stocks were independently studied. Severe lesions were seen in mice given HSV-2, or the restored virus designated HSV-2(R). Mice given ICP10ΔPK (RF or CS stocks) had no neurological symptoms nor skin lesions during the entire study protocol (days 1 through 21).

Immunizing a subject indicates the standard interpretation well known in the art. Upon administration of the vaccine composition, neutralizing antibodies and cell-mediated immunity are raised in the subject and said antibodies and cell-mediated immunity confer immunity to the subject.

The present invention teaches immunization of a subject against HSV-2. A "pfu" is a plaque forming unit and represents the quantity of virus required to form a single plaque when a cell culture is infected with the virus. It is a quantitative measure of viral infectivity used by those skilled in the art. A dose of 0.5–1 million pfu was used to immunize mice with ICP10ΔPK stock RF [ICP10ΔPK (RF)]. A dose of 1–10 million pfu was used to immunize mice with ICP10ΔPK stock CS [ICP10ΔPK (CS)]. The dosage range for a human is 1 to 100 million pfu. A preferred range is 1000 to 75 million pfu and an especially preferred range is 10,000 to 50 million pfu. Furthermore, due to the 50% homology of HSV-1 and HSV-2 there will be a high degree of protection against HSV-1 infection.

The formulation of ICP10ΔPK for human use is accomplished by suspension in a solution with or without stabilizing ingredients, and with or without immune stimulants and adjuvants. Examples of stabilizing agents, immune stimulants, and adjuvants. include alum, incomplete Freud's adjuvant, MR-59 (Chiron), MTPPE, MPL (monophosphoryl Lipid A). Such stabilizing agents, adjuvants and immune stimulants are well known in the art and can be used singly or in combination.

The vaccine composition of the present invention can be administered to any animal, including humans. The vaccine composition may be administered via any suitable mode of administration, such as intramuscular, oral, subcutaneous, intradermal, intravaginal, rectal, or intranasal administration. The preferred modes of administration are subcutaneous or intradermal administration.

The ICP10ΔPK which provides protection against HSV-2 infection can be administered along with a pharmaceutically acceptable carrier or diluent. Examples of such pharmaceutically acceptable carrier or diluents include water, phosphate buffered saline or sodium bicarbonate buffer. A number of other acceptable carriers or diluents are known.

DESCRIPTION OF THE PREFERRED EMBODIMENTS

It has been found that the recombinant strain ICP 10ΔPK(CS) is a preferred strain of Herpes Simplex type 2, which has had the gene coding for protein kinase deleted along with other unknown modifications of the genome which reduce its growth rate, for a vaccine for immunizing a human host against both HSV-1 and HSV-2. This strain exhibits the desirable characteristics of immunogenicity, latency without possessing toxicity or oncogenicity. This strain has been deposited on December 18, 1997, with the American Type Culture Collection (ATCC), 12301 Parklawn Drive, Rockville, Md. 20852, U.S.A., and is identified by the ATCC accession number, VR 2592.

The following examples are provided for illustrative purposes only and are in no way intended to limit the scope of the present invention.

Materials

Cells

Vero (African green monkey kidney) cells were grown in Eagle's minimum essential medium (EMEM) supplemented with 10% fetal calf serum (FCS) and antibiotics. JHLa1 cells (constitutively expresses ICP10) were previously described (Luo and Aurelian, J. Biol. Chem 267:9645–9653, 1992; Smith et al., Virology 200:598–612, 1994; Hunter et al., Virology 210:345–360, 1995). They were cultured in EMEM with 10% FCS, 1 mM Na pyruvate (GIBCO-BRL, Gaithersburg, Md.), 1× non-essential amino acids (GIBCO-BRL) and antibiotics. Vero-ICP10 cells were derived by transfection of Vero cells with an ICP10 expression vector that has a $SV_2$-neo cassette (pJW17N) (Luo and Aurelian, J. Biol. Chem 267:9645–9653, 1992; Smith et al., Virology 200:598–612, 1994). For serum starvation, cells grown to confluency in medium containing 10% FCS, were washed with phosphate-buffered saline (PBS) pH 7.0, and grown for two days in medium containing 0.5% FCS.

Plaque forming ability

Virus titers were determined by plaque assay as described (Aurelian, L, Herpes Simplex Viruses. In: *Clinical Virology Manual*, 2nd Edition. Specter, S. and Lancz, G., eds. Elsevier Science Pub. pp 473–494, 1992). Vero-ICP10 cells were used under an overlay consisting of MEM supplemented with 10% or 0.5% FCS and 0.3% IgG.

Antibodies

The production and specificity of the anti-LA-1 antibody specific for ICP10 amino acids 13–26 and monoclonal antibody (MAb 30) that recognizes a determinant in the ICP10 PK domain (amino acids 106–178) were previously described (Aurelian et al., Cancer Cells 7:187–191, 1989, Chung et al., J. Gen. Virol 72:1139–1144, 1991). ICP4 and ICP0 MAbs were purchased from Advanced Biotechnologies, (Columbia, Md.). Antibody C-11 to actin was purchased from Santa Cruz Biotechnology (Santa Cruz, Calif.).

Immunofluorescent Staining

Vero cells grown on 22 $mm^2$ glass cover slips (Corning Glass Works, New York) were infected with HSV-2 or ICP10ΔPK and fixed in cold methanol (−70° C.). They were stained (60 min, 37° C.) with anti LA-1 antibody or MAb 30 followed respectively by fluorescein-conjugated goat anti-rabbit or mouse IgG (Wymer et al., J. Virol. 63:277–2784, 1989, Smith et al., Virology 200:598–612, 1994).

EXAMPLE 1

Construction and Characterization of the ICP10ΔPK and HSV-2(R) viruses

The construction of the ICP10ΔPK virus has been described (Peng et al., Virology 216:184–196, 1996). Briefly, the wild type sequences in a plasmid (TP 101) that contains the HSV-2 BamHI E and T fragments were replaced with the 1.8kb SalI/BglII fragment from pJHL9 [ICP10 mutant deleted in the PK domain (Luo and Aurelian, J. Biol. Chem. 267:9645–9653, 1992)]. The resulting plasmid, TP9, contains sequences which code for ICP10 deleted in the PK domain flanked by 4 and 2.8 kb of HSV-2 DNA sequences at the 5' and 3' ends, respectively. The 10 kb HindIII/EcoRI fragment from TP9 was introduced by marker transfer into a virus (ICP10ΔRR) in which the RR domain of ICP10 had been replaced with the LacZ gene. The resulting recombinant virus, designated ICP10ΔPK, was obtained by selecting white plaques on a background of blue plaques after staining with X-gal. A few white plaques were picked and purified. Two stocks were grown in Vero cells in MEM with 10% FCS (exponential). They were respectively designated ICP10ΔPK (RF) and ICP10ΔPK (CS). For the construction of the restored virus HSV-2(R), Vero cells were co-transfected with 1 μg of infectious viral DNA from ICP10ΔPK and a 10-fold molar excess of the wild type BamHI E/T fragment. A strategy similar to that reported for ICP6Δ (Goldstein and Weller, Virology 166:41–51, 1988) was used to select restored virus under growth restricted conditions (serum starved Vero cells).

Southern blot hybridization was used to confirm that the ICP10ΔPK DNA is deleted in the ICP10 PK coding region. Generally, viral DNA was isolated from cytoplasmic virions as described (Pignatti et al., Virology 93:260–264, 1979; Smith et al., J. Gen. Virol. 73:1417–1428, 1992). Briefly, Vero cells were infected at a multiplicity of infection (moi) of 5. At 48 hrs. p.i. cells were resuspended (2×$10^7$ cell/ml) in a buffer consisting of 10 mM Tris-HCl (pH 7.9), 10 mM EDTA and 0.25% Triton. Following incubation on ice (15 min.), NaCl was added at a final concentration of 0.2 M and the nuclei were precipitated by centrifugation at 1,000× g (10 min, 4° C.). The supernatant, containing cytoplasmic virions, was incubated in 200 μg/ml Proteinase K and 0.2% SDS (4 hr at 37° C.), mixed with saturated sodium iodide (NaI; final concentration 1.525 g/ml) and ethidium bromide (final concentration 3 μg/ml) and centrifuged at 100,000×g for 16 hrs.

Viral DNA (15 μg) was digested with BamHI and the fragments were separated by 1% agarose gel electrophoresis in a Tris-Acetate EDTA (TAE) buffer (40 mM Tris-acetate and 1 mM EDTA). It was transferred to Gene screen membranes (New England Nuclear Corp.) and the membranes were incubated in a prehybridization solution containing 5×SSC [750 mM NaCl, 75 mM Sodium citrate; pH (7.0)], 2% Casein, 0.1% N-laurylsarcosine and 0.02% sodium dodecyl sulfate (SDS) at 42° C. for 2 hrs. The hybridization probe was oligonucleotide AU26

(CCCCTTCATCATGTTTAAGGA) which represents a sequence in the ICP10 RR coding region. It was 3' tailed with digoxigenin-dUTP (DIG-dUTP) by terminal transferase (Boehringer Mannheim) in 20 μl volume with 1× reaction buffer [5 mM cobalt chloride ($CoCl_2$), 0.05 mM DIG-dUTP, 5 nmol/ml AU26, 0.5 mM dATP and 2.5 units/μl terminal transferase] at 37° C. for 15 min. diluted to a final concentration of 5 pmol/ml in prehybridization solution. Hybridization was done at 42° C. for 3 hrs. Membranes were washed once (room temperature) in a solution containing 2×SSC, 0.1% SDS for 5 mins and twice in 0.5×SSC, 0.1% SDS for 15 mins. For detection of the hybridized DNA fragments, the membranes were rinsed in Buffer 1 (100 mM Tris-HCl, pH 7.5, 150 mM NaCl), incubated in Buffer 2 [2% (w/v) casein in Buffer 1] for 40min and in Buffer 2 containing $3×10^{-4}$ U/ml of alkaline phosphatase-conjugated anti-digoxigenin antibody (Boehringer Mannheim) for 30 min. After washing with Buffer 1 (twice) and soaking in Buffer 3 (100 mM Tris-HCl, pH 9.5, 100 mM NaCl, 50 mM $MgCl_2$) for 2 min, the membranes were exposed to the chemiluminescent substrate Lumi-Phos™ 530 (Boehringer Mannheim) and the reaction was developed on X-ray film.

More specifically, DNA (15 μg) from HSV-2, ICP10ΔPK or HSV-2(R) was digested with BamHI, separated on 1% agarose gels and transferred to nylon membranes. It was hybridized with the AU26 probe which recognizes a sequence within the ICP10RR coding region (FIG. 1A). A hybridizing 7.6kb band which represents the BamHI E fragment was observed for HSV-2, (FIG. 1B, lane 2) and HSV-2(R) (FIG. 1B, lane 3) DNA. The hybridizing band seen for ICP10ΔPK DNA was 2.2 kb (FIG. 1B, lane 1) consistent with the expected size. Similar results were obtained for ICP10ΔPK (RF) and ICP10ΔPK (CS). The data confirm that ICP10ΔPK DNA is deleted in the PK coding region.

EXAMPLE 2

Expression of the 95kDa PK deleted ICP10 protein (p95)

To determine whether ICP10ΔPK expresses an ICP10 protein deleted in its PK domain, Vero cells were infected with ICP10ΔPK (200 pfu/cell) and labeled with [$^{35}$S]-methionine (100 μCi/ml) from 6–16 hrs p.i. Cells infected with HSV-2 or HSV-2(R) served as controls. Generally, cells were mock-infected with PBS (pH7.4) or infected with 200 PFU/cell of HSV-2, ICP10ΔPK, or HSV-2 (R). They were labeled with [$^{35}$S]-methionine (100 μCi/ml) (sp Act 1120 Ci/mmol, Dupont, NEN Research Products) in EMEM containing no methionine and 10% dialyzed FCS. In some experiments, infection was done in the presence of cycloheximide (50 μg/ml) for 6 hr at which time cycloheximide was removed, cells were washed extensively with PBS, and incubated (3 hrs) in the presence of 10 μg/ml actinomycin D and 100 μCi/ml of [$^{35}$S]-methionine. For immunoprecipitation, cell lysates were incubated in cold RIPA buffer [0.01 M Tris-HCl (pH 8.0), 0.1% SDS, 1% Nonidet P40, 1% deoxycholate, 0.15 M NaCl, 1 mM dithiothreitol] with 1 mM phenylmethylsulfonyl fluoride (PMSF), 100 Kallikrein units/ml aprotinin (Sigma) for 15 min on ice, and cleared of cell debris by centrifugation for 30 min at 20,000×g. They were incubated with 15–20 μl of antibody (1 hr, 4° C.) and 100 μl protein A-Sepharose CL4B beads [10 mg in 0.1 M Tris-HCl (pH 8.0), 0.15 M NaCl and 0.5% Nonidet P40] (30 mins, 4° C.). Beads were washed extensively with ice-cold RIPA buffer and bound proteins were eluted by boiling (5 min) in 100 μl denaturing solution [150 mM Tris hydrochloride (pH 7.0), 5.7% SDS, 14% 2-mercaptoethanol, 17% sucrose and 0.04% bromothymol blue].

Proteins were resolved by SDS-PAGE on 7% or 8.5% polyacrylamide gels and visualized by autoradiography. In some experiments, cells were resuspended directly into denaturing solution, boiled for 5 min., and analyzed by SDS-PAGE.

More specifically, cell extracts were precipitated with anti-LA-1 antibody and the proteins were resolved by SDS-PAGE on 7% polyacrylamide gels. Anti-LA-1 antibody precipitated a 140 kDa protein from HSV-2 (FIG. 2A, lane 1) or HSV-2(R) (FIG. 2A, lane 3) infected cells. From ICP10ΔPK infected cells, it precipitated a 95kDa protein (p95) (FIG. 2A, lane 2) which is consistent with the PK deleted ICP10 (Luo and Aurelian, J. Biol. Chem. 267:9645–9653, 1992). The preimmune serum was negative (FIG. 2A, lane 4). A 38 kDa protein consistent with RR2 was co-precipitated by anti-LA-1 antibody from cells infected with all three viruses indicating that p95 can complex with RR2, presumably at the carboxy terminus previously implicated in complex formation (Chung et al., J. Gen. Virol. 72:1139–1144, 1991). Similar results were obtained for ICP10ΔPK (RF) and ICP10ΔPK (CS):

EXAMPLE 3 p95 Expressed By ICP10ΔPK Lacks Kinase Activity

We have previously shown that: (i) ICP10 has kinase activity in HSV-2 infected and stably transfected cells, and (ii) PK activity is associated with the 57–60 kDa amino terminal domain of the ICP10 protein, but not with its 90–95kDa carboxy terminal domain (Chung et al., J. Virol. 63:3389–3398, 1989; Smith et al., Virology 200:598–612, 1994). To determine whether p95 expressed by ICP10ΔPK has PK activity, extracts of cells infected with HSV-2, ICP10ΔPK or HSV-2(R) (moi=200, 16 hrs p.i.) were immunoprecipitated with anti-LA-1 antibody and subjected to PK assays (Chung et al., J. Virol. 63:3389–3398, 1989).

Generally, immunoprecipitates of cell extracts normalized for protein concentration by the BCA protein assay kit, (PIERCE, Rockford, Ill.) were washed with TS buffer containing 20 mM Tris-HCl (pH 7.4), 0.15 M NaCl, suspended in 50 μl of kinase reaction buffer consisting of 20 mM Tris-HCl (pH 7.4), 5 mM $MgCl_2$, 2 mM $MnCl_2$ and 10 μCi of [32p] ATP (3000 Ci/mmol, Dupont, New England Research Product), and incubated at 30° C. for 15 min (Chung et al., J. Virol 63:3389–3398, 1989; Chung et al., Virology 179:168–178, 1990; Smith et al., J. Gen. Virol. 73:1417–1428, 1992; Smith et al., Virology 200:598–612, 1994; Peng et al., Virology 216:184–196, 1996). The beads were washed once with 1 ml TS buffer, resuspended in 100 μl of denaturing solution and boiled for 5 min. The proteins were resolved by SDS-PAGE on 7% polyacrylamide gels as described (Chung, et al., J. Virol. 63:3389–3398, 1989). Proteins were electrotransferred onto nitrocellulose membranes as previously described (Aurelian et al., Cancer Cells 7:187–191, 1989) and immunoblotting was performed by incubation with the respective antibodies followed by protein A-peroxidase (Sigma) for 1 hr at room temperature each. Detection was with ECL reagents (Amersham, Chicago, Ill.), as described (Smith et al., Virology 200:598 612, 1994).

More specifically, the resolved proteins were transferred to a nitrocellulose membrane and immunoblotted with anti- LA-1 antibody to determine the levels of protein in the precipitates. The 140 kDa ICP10 protein from HSV-2 (FIG. 2B, lane 1) or HSV-2(R) (FIG. 2B, lane 3) infected cells was phosphorylated. A phosphorylated 95 kDa protein was not seen in cells infected with ICP10ΔPK (FIG. 2B, lane 2). This is not due to low levels of protein in the precipitates used for PK assay, because similar protein levels were seen for all three viruses by immunoblotting with anti LA-1 antibody (FIG. 2C). A phosphorylated 38kDa protein was seen in HSV-2 (FIG. 2B, lane 1) and HSV-2(R) (FIG. 2B, lane 3) infected cells but not in cells infected with ICP10ΔPK (FIG. 2B, lane 2). Preimmune serum was negative (FIGS. 2B,C, lane 4). We interpret these data to indicate that RR2 is phosphorylated by ICP10 PK, as previously reported by Chung et al., (J. Virol 63:3389–3398, 1989) and Peng et al. (Virology 216:1 196, 1996). It is not phosphorylated by p95, consistent with the absence of the PK domain. Similar results were obtained for ICP10ΔPK (RF) and ICP10ΔPK (CS). The data confirm that the ICP10 PK coding region is required for kinase activity, also within the context of virus infection.

EXAMPLE 4

Ribonucleotide Reductase Activity of ICP10ΔPK

It is generally believed that the RR and PK activities of the RR1 protein can be dissociated (Ingemarson et al., Virology 156:417–422, 1987; Chung et al., J. Virol. 63:3389–3398, 1989). To examine the validity of this interpretation it is important to document whether the loss of ICP10 PK activity has any effect on RR activity. RR assays were performed on extracts from infected cells (moi=20, 16 hrs, p.i.). RR activity was assayed as described (Smith et al., J. Gen Virol. 73:1417–1428, 1992). Extracts from 16 hrs infected cells or mock infected cells were resuspended in HD buffer [100 mM HEPES buffer (pH 7.6), 2 mM dithiothreitol (DTT)] at 2×10$^7$ cell equivalents/ml, incubated on ice for 15 mins, disrupted by sonication (30–60 secs at maximum setting; Ultrasonics model 220F Sonifier) and clarified of cell debris by centrifigation (100,000×g; 1 hr, 4° C.). The HSV RR activity was precipitated with crystalline ammonium sulfate [45% saturation (0.258 g/ml)]. Following dialysis and centrifugation (16,000 ×g; 30 min), the partially purified enzyme preparations were incubated (37° C.; 10 min) with equal volumes of a 2× standard reaction mixture containing 400 mM HEPES buffer (pH 8.0), 20 mM DTT and 0.2 mM [$^3$H]-CDP (17.8 Ci/mmol, Amersham, Ill.). The reaction was terminated by the addition of 100 mM hydroxyurea with 10 mM EDTA (pH 8.0) and boiling for 3 min. *Crotalus atrox* venom (Sigma, St Louis, Mo.) was added [0.5 mg/ml in 12 mM Tris HCl (pH 9.0), 4 mM MgCl$_2$, 1 mM deoxycytidine) and the mixture was incubated 30 min at 37° C., boiled for 3 min and applied to a 0.5 ml Dowex-1 borate column (Sigma). The column was washed with 2.5 ml H$_2$O and 0.5 ml eluate fractions were mixed with Biofluor (New England Nuclear, Boston, Mass.) for scintillation counting. Ribonucleotide reductase activity is expressed as units/mg, where 1 unit represents the conversion of 1 nmol [$^3$H]-CDP to dCDP/hr/mg protein.

More specifically, as shown in Table 1, the ICP10ΔPK virus had a similar RR activity as that of HSV-2 and HSV-2(R). This is consistent with the finding that p95 coprecipitates with RR2 and supports the conclusion that the PK and RR activities can be functionally dissociated.

TABLE 1

Ribonucleotide reductase activity of ICP10ΔPK virus.

| Virus | cpm[a] | RR Specific activity (Units)[b] |
|---|---|---|
| HSV-2 | 11,534 | 10.2 |
| HSV-2(R) | 10,037 | 8.8 |
| ICP10ΔPK (RF) | 9,540 | 8.4 |
| Mock-infected | 3,060 | 2.7 |

[a]cpm/270 mg protein
[b]One RR unit = conversion of 1 nmol CDP to dCDP/h/mg protein.

EXAMPLE 5

Growth Properties of ICP10ΔPK

The growth properties of ICP10ΔPK were studied under exponential (10% serum) and growth restricted (0.5% serum) conditions. In a first series of experiments, Vero cells were infected with HSV-2, ICP10ΔPK (RF), or HSV-2(R) at moi of 2 and virus growth examined for 36 hrs p.i. As shown in FIG. 3, HSV-2 grew equally well under exponential and growth restricted conditions. Virus replication began at 2 hrs p.i. and reached peak levels at 36 hrs p.i. (burst size 1000 pfu/cell). A similar growth pattern was evidenced by HSV-2(R). By contrast, onset of ICPlIOΔPK replication was not seen until 15 hrs p.i. both in exponential and serum starved cells. At that time replication resumed, reaching titers similar to those of HSV-2 at 36hrs p.i. in exponential cells (burst size 1000 pfu/cell), but not in serum starved cells (burst size 1 pfu/cell).

In a second series of experiments, exponential Vero cells were infected with HSV-2, or ICP10ΔPK (RF) at moi of 200. HSV-2 replication began at 2 hrs p.i. and reached maximal titers at 20 hrs p.i. (FIG. 4A). By contrast, replication of ICP 10ΔPK virus was first seen at 10–12 hrs p.i., with maximal titers at 36hrs p.i. (FIG. 4B). The growth of HSV-2(R) was virtually identical to that of HSV-2 (data not shown). The titers of intracellular and extracellular virus were similar for HSV-2, ICP10ΔPK and HSV-2(R), indicating that progeny virus was released equally well (FIG. 4).

Virus growth was next compared for the two ICP10ΔPK virus stocks. Exponential Vero cells were infected with ICP10ΔPK (RF) or ICP10ΔPK (CS) at moi's of 2 or 200 pfu/cell. In cells infected at moi of 2 pfu/cell ICPI0ΔPK (RF) replication began at 15 hrs p.i. By contrast replication of ICP10ΔPK (CS) did not begin until 20 hrs p.i., suggesting that it was more defective (FIG. 5A). For both virus stocks, peak titers were seen at 35 hrs p.i. Those of ICP10ΔPK (RF) were 1000 pfu/cell. Those of ICP10ΔPK (CS) were 780 pfu/cell (FIG. 5A). In cells infected at moi of 200 pfu/cell, ICP10ΔPK (RF) replication began at 11 hrs p.i. By contrast replication of ICP10ΔPK (CS) did not begin until 15 hrs p.i., demonstrating a delay in the onset of virus replication proportional to that seen in cells infected at low moi (FIG. 5B). For both virus stocks, peak titers were seen at 35 hrs p.i. They were 580 and 50 pfu/cell for ICP10ΔPK (RF) and ICP10ΔPK (CS) respectively (FIG. 5B). Because the ICP10ΔPK (RF) and ICP10ΔPK (CS) virus stocks were similarly constructed and both lack ICP10 PK activity but retain RR activity, we conclude that their different growth patterns reflect additional differences which were presumably acquired during growth amplification and account for the further attenuation of ICP10ΔPK (CS).

To confirm that ICP10 PK is indeed required for virus replication, we also examined virus growth in JHLa1 cells that constitutively express ICP10. 293 cells which were used to establish the JHLa1 line were used as control (Luo and Aurelian, J. Biol. Chem 267:9645–9653, 1992; Smith et al., Virology 200:598–612, 1994; Hunter et al., Virology 210:345–360, 1995). Cells were infected at moi of 200 and overlaid with MEM-1% FCS. ICP10ΔPK growth in 293 cells was similar to that seen in Vero cells in that newly synthesized virus was not seen before 10 hrs p.i. (FIG. 6B). By contrast, in JHLa1 cells, ICP10ΔPK grew as well as HSV-2, with replication first seen at 2 hrs p.i. and reaching maximal levels at 20 hrs p.i. (burst size; 2800 and 2500 for HSV-2 and ICP10ΔPK respectively) (FIG. 6A). Similar results were obtained for ICP10ΔPK (RF) and ICP10ΔPK (CS). We interpret these findings to indicate that ICP10 PK is required for virus replication both in exponential and growth restricted cells. However a compensatory function(s) seen in both Vero and 293 cells is responsible for the resumption of virus growth at 10–15 hrs p.i. Because the growth of ICP10ΔPK virus resumed earlier in cells infected at high moi than low moi, but the burst size was significantly higher in exponential than in serum starved cells (1000 vs 1 respectively) we assume that the compensatory function is a cellular Ser/Thr PK induced by incoming virus structural protein(s).

EXAMPLE 6

ICP10ΔPK and HSV-2 Have Similar Cell Adsorption Kinetics

One possible interpretation for the growth pattern evidenced by ICP10ΔPK is that it is defective in its ability to adsorb/penetrate the cells. To address this question, Vero cells were exposed to 200 pfu of HSV-2, ICP10ΔPK, or HSV-2(R) for 0, 10, 30, 60, 90 or 120 minutes. They were extensively washed with PBS, overlayed with MEM-10% FCS and 0.3% IgG and reincubated at 37° C. for 48 hrs. At this time they were scored for plaque formation. As shown in FIG. 7, the number of plaques increased for all three viruses as a function of exposure time, reaching maximal levels at 20–30 min. and plateauing thereafter. Virus titers in the original inocula decreased in parallel, with similar patterns seen for HSV-2, ICP10ΔPK, and HSV-2(R) (data not shown). Similar results were obtained for ICP10ΔPK (RF) and ICP10ΔPK (CS).

EXAMPLE 7

Plaque Forming Ability of ICP10ΔPK Virus

To analyze the plaque forming ability of ICP10ΔPK we used Vero and Vero-ICP10 cells grown in 10% or 0.5% serum. Consistent with the low burst size observed in serum starved cells infected at low moi, ICP10ΔPK plaque forming ability was severely compromised in serum-starved Vero cells. Virus titers were similar to those of HSV-2 in exponentially growing Vero cells (10% serum) and in Vero-ICP10 cells (Table 2). In Vero cells (grown in 10% or 0.5% FCS), ICP10ΔPK plaques were hazy, apparently reflecting incomplete cell lysis. The extent of cell lysis differed somewhat from one experiment to the next, but it was never as complete as that seen for HSV-2. The plaques of ICP10ΔPK (CS) were smaller than those of ICP10ΔPK (RF), consistent with the conclusion that its growth was more severely compromised. The morphology of the ICP10ΔPK plaques in Vero-ICP10 cells and that of HSV-2 (R) plaques in all cells was similar to that of HSV-2 (data not shown).

TABLE 2

Plaquing efficiency of ICP10ΔPK virus in dividing and serum starved cells

| Virus | Cells (+/− serum)[a] | Virus Titer[b] (wt/mutant) |
| --- | --- | --- |
| HSV-2 | Vero (+) | $5.0 \times 10^7$ |
| ICP10ΔPK (RF) | Vero (+) | $2.8 \times 10^7$ (1.8) |
| HSV-2 | Vero (−) | $4.7 \times 10^7$ |
| ICP10ΔPK (RF) | Vero (−) | $3.5 \times 10^4$ ($1.3 \times 10^3$) |
| HSV-2 | Vero-ICP10 (+) | $4.9 \times 10^7$ |
| ICP10ΔPK (RF) | Vero-ICP10 (+) | $2.2 \times 10^7$ (2.2) |
| HSV-2 | Vero-ICP10 (−) | $4.6 \times 10^7$ |
| ICP10ΔPK (RF) | Vero-ICP10 (−) | $2.0 \times 10^7$ (2.3) |

[a]plaque assays done in medium containing 10% serum (+) or 0.5% serum (−).
[b]plaque forming units/ml

EXAMPLE 8

IE Protein Expression is Inhibited in ICP10ΔPK Infected Cells Early in Infection The growth defect of ICP10ΔPK virus may reflect its failure to initiate protein synthesis. To address this possibility, Vero cells were mock infected or infected with HSV-2, ICP10ΔPK, or HSV-2(R) (moi=200) for 2 or 7 hrs, pulse labeled with [$^{35}$S]-methionine for an additional 60 min., and proteins were resolved by SDS-PAGE. The protein profiles in HSV-2 infected cells were similar to those previously described (Wilcox et al., J. Virol 33:167–182, 1980) and included, at 3 hrs p.i, ICP4, ICP0, ICP10, and ICP27 (FIG. 8A, lane 2). Similar protein profiles were seen in cells infected with HSV-2(R) (FIG. 8A, lane 8). By contrast, the protein profiles in cells infected with ICP10ΔPK for 3 hrs (FIG. 8A, lane 3) resembled those in mock infected cells (FIG. 8A, lane 1). The exception were two bands, 110 kDa and 95 kDa (FIG. 8A, lane 3) which were respectively recognized by ICP0 and ICP10 antibodies in immunoblotting (FIG. 8B, lanes 1,2). Densitometric scanning indicated that the levels of ICP0 were 4-fold lower in ICP 1 0ΔPK than HSV-2 [or HSV-2(R)] infected cells (3130 and 782 units for HSV-2 and ICP 1OΔPK respectively) and the p95 levels (in ICP10ΔPK infected cells) were 7-fold lower than the ICP10 levels in HSV-2 and HSV-2(R) infected cells (3567 and 480 units for ICP10 and p95 respectively). In cells infected with ICP10ΔPK for 8 hrs, the levels of ICP0 and p95 were higher, and bands consistent with ICP4, ICP5, and ICP27 were detected (FIG. 8A, lane 5). The identity of the ICP4 band in 8 hrs infected cells was confirmed by immunoblotting with ICP4-specific MAb (FIG. 8B, lane 3). The protein profile in ICP10ΔPK infected cells at 12 hrs p.i. (FIG. 8A, lane 6) was similar to that of HSV-2 infected cells at 8 hrs p.i. (FIG. 8A, lane 4). These findings indicate that viral proteins other than ICP0 and p95 are not expressed in cells infected with ICP10ΔPK for 3 hrs, suggesting that ICP10 PK is required for expression of IE proteins ICP4, ICP22 and ICP27. Indeed the protein profile in ICP10ΔPK infected JHLa1 cells (supply ICP10 PK activity) at 3 hrs. p.i. is virtually identical to that of HSV-2 infected cells (FIG. 8A, lane 7). Because these three IE proteins are responsible for the regulation of early and late viral gene expression (Sacks et al., J. Virol 55:796 05, 1985; McCarthy et al., J. Virol. 63:18–27, 1989; Samaniego et al., J. Virol. 69:5705–5715, 1995; Dixon and Schaffer, J. Virol 36:189–203, 1980; Rice et al., J. Virol. 69:5550–5559, 1995; Leopardi and Roizman, Proc. Natl. Acad. Sci. USA 93:4562 576, 1996), their absence from ICP10ΔPK infected cells results in complete inhibition of viral protein synthesis and infectious virus production.

To further examine the synthesis of IE proteins in ICP10ΔPK infected cells, infection was done in the presence of 50 μg/ml cycloheximide (6 hr) and cells were labeled with [35S]-methionine for 3 hrs in medium containing 10 μg/ml of actinomycin D, conditions that allow IE gene expression but not expression of other viral genes (Honess and Roizman, J. Virol. 14:8–19, 1974; Strnad and Aurelian, Virology 73:244–258, 1976). Proteins consistent with ICP4, ICP10, ICP0, ICP22, and ICP27 were seen in HSV-2 infected cells (FIG. 9A, lane 2). By contrast, ICP4, ICP10, ICP22 and ICP27 were not seen in ICP10ΔPK infected cells (FIG. 9A, lane 3). A 10 kDa protein, consistent with ICP0, and a 95 kDa protein, consistent with p95, were seen in ICP10ΔK infected cells (FIG. 9A, lane 3), but their levels were respectively 2-fold and 3-fold lower than in HSV-2 infected cells (FIG. 9A, lane 2) (densitometric integration units 1760 and 3520 for ICP0; 733 and 2200 for p95 and ICP10, in ICP10ΔPK and HSV-2 infected cells, respectively). Immunoblotting confirmed that the 110 kDa and 95 kDa proteins were ICP0 and p95 respectively (FIG. 9B, lanes 1,2). The protein profiles for HSV-2(R) were similar to those for HSV-2 (data not shown). These data support the conclusion that ICP10 PK is required for expression of ICP4, ICP22, and ICP27, but not ICP0 and p95.

EXAMPLE 9

ICP10ΔPK Virus is Defective for ICP4 Transcription.

Northern hybridization was used to examine whether the failure to detect ICP4 in ICP10ΔPK infected cells is due to a transcriptional defect. RNA was obtained from Vero cells infected with HSV-2, ICP10ΔPK (RF) or HSV-2(R). ICP4 or ICP0 DNA were used as probes. GAPDH served as control transcript. The guanidinium isothiocyanate/cesium chloride gradient method was used to isolate and purify RNA from Vero cells infected with HSV-2, ICP10ΔPK or HSV-2(R) (moi =200). Northern blot hybridization was done as described (Feng et al., Antisense Nucleic Acid Development 6:25–35, 1996). Hybridization was for 16 hrs at 42° C. with [$^{32}$P]-labeled ICP4, ICP0 or GAPDH probes in a solution containing 40% formamide, 6xSSPE, 2xDenhardt's, 0.1% SDS, and 250 μg/ml salmon sperm DNA. The ICP4 probe was a 1.9 kb BamHI DNA fragment derived from pXhol-C. The ICP0 probe was a 1.7 kb NruI-SalI fragment derived from pIGA15 (O'Hare and Hayward, J. Virol. 53:751–760, 1985). The human GAPDH probe was a 40-mer oligonucleotide purchased from Oncogene Science (Cat No. ON407). The probes were [$^{35}$P]dCTP labeled by the random priming method using an oligonucleotide kit (Pharmacia, Uppsala, Sweden) according to manufacturer's instructions. Blots were washed twice in 2xSSC-0.1% SDS and twice in 0.1xSSC-0.01% SDS for 10 min. each at ambient temperature followed by one wash in 0.1xSSC-0.1% at 50° C. and visualized by autoradiography. The relative abundance of ICP4 and ICP0 mRNA was estimated by first normalizing to the value of GAPDH mRNA in each sample.

Both ICP4 and ICP0 mRNA were seen in Vero cells infected with HSV-2 (FIG. 10A, lanes 1,2) or HSV-2(R) (FIG. 10A, lanes 5,6) for 3 hrs. The kinetics of ICP4 expression in HSV-2 infected cells were similar to those previously described for HSV-1 infected cells. Optimal levels were seen at 3 hrs p.i. (FIG. 10C, lane 2) and the transcript was no longer detectable at 8 hrs p.i. (FIG. 10C, lane 4). By contrast, ICP4 mRNA was not seen in cells infected with ICP10ΔPK for 3 hrs (FIG. 10A, lane 3). However, by 8 hrs p.i. (FIG. 10B, lane 3), its levels were similar to those seen earlier (at 3hrs p.i.) in HSV-2 infected cells (FIG. 10C, lane 2). The transcript was no longer seen at 20 hrs p.i. (FIG. 10B, lane 6). Cells infected with ICP 1 0ΔPK for 3 hrs were positive for ICP0 mRNA (FIG. 10, lane 4), but its relative abundance (expressed as ICP0/GAPDH mRNA) was 3-fold lower than in HSV-2 infected cells (0.32 and 1.0 respectively). The data indicate that ICP10 PK is required for early transcription of ICP4 and contributes to optimal transcription of ICP0.

EXAMPLE 10

ICP10 PK plays a role in inhibition of host cell gene expression and cell lysis.

The morphology of the ICP10ΔPK plaques is consistent with incomplete cell lysis. Because ICP27 plays a role in the shut-off of host protein synthesis (Hardwicke et al., J. Virol 68:4797–4810, 1994) and it is not expressed in cells infected with ICP10ΔPK for 8–12 hrs p.i., we also examined the expression of a host cell gene (actin) in cells infected with HSV-2 or ICP10ΔPK. Vero cells were mock infected or infected with HSV-2 or ICP10ΔPK at moi of 200 and assayed for actin expression by immunoblotting with anti-actin antibody. Actin was not seen in HSV-2 infected cells as early as 3 hrs p.i. (FIG. 8C, lane 2). By contrast, actin levels in cells infected with ICP10ΔPK (FIG. 8C, lane 3) were similar to those in mock infected cells (FIG. 8C, lane 1) as late as 12 hrs p.i. These findings are consistent with the observation that cytopathogenic effect (CPE) is not seen in ICP10ΔPK infected cells until 15–20 hrs p.i. when the compensatory function(s) come into play.

EXAMPLE 11

Intracellular Localization of ICP10 and p95 Proteins

Previous studies of cells infected with HSV-2 for 8 and 12 hrs had shown that ICP10 localizes in the cytoplasm and is also associated with the cytoskeleton (Chung et al., J. Virol 63:3389–3398, 1989). However cells infected for less than 8 hrs were not studied. Because ICP10 PK is required for IE gene expression before 8 hrs, the question arises whether at that time it is also present in the nucleus. Vero cells infected with HSV-2 or HSV-2(R), for 3,6, or 9 hrs were stained in immunofluorescence with MAb30 (recognizes ICP10 amino acids 106–178). Cells similarly infected with ICP10ΔPK were stained with anti LA-1 antibody (recognizes ICP10 amino acids 13–26). Strong intranuclear staining was seen in cells infected with HSV-2 for 3 hrs (FIG. 11A). It had a punctate appearance consisting of discrete spherical structures (granules) similar to those previously described for viral replication compartments (Rice et al., J. Virol 68:988–1 001, 1994; Mullen et al., J. Virol. 68:3250–3266, 1994). At later times p.i., staining took the characteristic perinuclear and diffuse cytoplasmic pattern previously described for ICP10 (FIGS. 11B,C). Similar staining patterns were seen for HSV-2(R) (data not shown). By contrast, in ICP10ΔPK infected cells, staining was not seen before 9 hrs p.i. (FIGS. 11D,E), at which time it was localized only in the cytoplasm (FIG. 11F). Nuclear staining was also not seen in ICP10ΔPK infected cells at 12 or 15 hrs p.i. (data not shown). These findings suggest that the PK domain of ICP10 is required for nuclear localization early in infection (before 6 hrs).

EXAMPLE 12

ICP10ΔPK virus is attenuated for growth in infected animals

We used the mouse footpad model of HSV-2 infection, in order to examine the role of ICP10ΔPK in virus growth in vivo. Swiss-Webster mice were inoculated s.c. in the footpad with $5\times10^6$ pfu of HSV-2, ICP10ΔPK(RF) or a restored virus designated HSV-2(R). Neurological symptoms and severe skin lesions were seen in mice given HSV-2 or HSV-2(R), beginning on day 6 p.i. ICP10ΔPK infected mice had no neurological symptoms nor skin lesions. HSV-2 and HSV-2(R) were isolated from the footpad and ganglionic homogenates for 7–9 days p.i. ICP10ΔPK was only isolated for 4 days p.i. Maximum titers were lower for ICPlOΔPK than HSV-2 ($4.3\times10^4$ and $3\times10^7$ pfu for ICP10ΔPK and HSV-2 respectively), and the proportion of latently infected ganglia yielding virus was 90% and 80% for HSV-2 and HSV-2(R) as compared to 10% for ICP10ΔPK (Table 3). These data suggest that ICP10PK is involved in acute infection and directly or indirectly, in latency reactivation/establishment.

TABLE 3

Growth and latency reactivation of ICP10ΔPK virus

| Virus | Mean virus titer in footpads[a] (pfu/ml) | | | | Latency[c] (%) |
|---|---|---|---|---|---|
| | Day 2 | Day 3 | Day 4 | Day 7 | |
| HSV-2 | $1.5\times10^3$ (+)[b] | $2\times10^4$ (+) | $3\times10^7$ (+) | $1\times10^7$ (+) | 9/10 (90) |
| HSV-2(R) | ND | $2\times10^4$ (+) | ND | $6.1\times10^6$ | 8/10 (80) |
| ICP10ΔPK (RF) | $6.3\times10^3$ | $2.5\times10^3$ (+) | $4.3\times10^4$ (+) | — | 1/10 (10) |

[a]Mice (n = 10) were infected with $5\times10^6$ pfu in the footpad. Virus titers were determined by plaque assay. Lesions were seen beginning on day 7 in HSV-2 and HSV-2(R) infected mice.
[b]Ganglia were obtained on days 3 and 5 p.i., homogenized and assayed for virus. (+) means virus was isolated; (−) means virus was not isolated
[c]Latency is no. of explanted ganglia positive for virus at 30 days p.i./no. tested
ND = not done

EXAMPLE 13

ICP10ΔPK Virus Protects from HSV-2 Challenge

Two groups of 10 mice each were respectively mock-infected with phosphate buffered saline (PBS) or ICP10PK (RF) ($5\times10^5$ to $1\times10^6$ pfu) by one sc injection in the footpad. They did not develop any visible symptoms. On day 16 p.i. they were challenged with $1\times10^7$ pfu of HSV-2 All mice in the PBS group developed lesions consisting of swelling and redness, first visible on day 5 p.i. and virus (HSV-2) was isolated from the footpads of 10/10 infected mice. On day 15 p.i., 5/10 (50%) of the mice in the PBS group developed paralysis. Mice immunized with ICPlOΔPK virus did not develop visible lesions after HSV-2 challenge. Virus was isolated from the footpad in 3/10 (30%) animals. Virus was not isolated from the footpads of 7/10 (70%) of the ICP10ΔPK immunized mice.

TABLE 4

Protection mediated by ICP10ΔPK

| Immunization | Lesions | Challenge | Lesions | Virus isolation |
|---|---|---|---|---|
| PBS | None | HSV-2 ($1\times10^7$) | 10/10 | 10/10 |
| ICP10ΔPK (RF) | None | HSV-2 ($1\times10^7$) | 0/10 | 3/10 |

Mice (groups of 10) were immunized with PBS or ICP10ΔPK (one sc injection) and challenged with HSV-2 in the footpad These findings indicate that immunization with relatively low doses of ICP10ΔPK protects from challenge with high doses of HSV-2. There is absolute protection in terms of lesion development, in that skin lesions were seen in all unimmunized mice as compared to no lesions in immunized mice. Non-immunized mice were not protected from virus replication, with virus being isolated from all animals on day 5 post challenge. Immunized mice were protected, with virus being isolated from only 3/10 (30%) of the animals. The absence of detectable lesions in the 3 animals from which virus was isolated, presumably reflect relatively low titers, suggesting that even though immunization did not afford a 100% level of protection, it reduced the titers of the challenge virus.

EXAMPLE 14

ICP10ΔPK Virus Induces HSV Specific Immunity

Two groups of 4 mice each were immunized with HSV-2 or ICP10ΔPK(RF) ($1\times10^6$ pfu) by sc injection in the footpad. On day 24 p.i., spleens were removed and T cells were used in lymphocyte proliferation assay with HSV-2 antigen as we previously described (Wachsman, et al., Bioscience Reports, 8:323 334, 1985; Wachsman, et al., J. Inf. Dis. 159:625 34, 1989; Wachsman, et al., Vaccine 10:447454, 1992). This assay measures the development of HSV-specific memory. Uninfected cell extracts prepared in parallel to the virus antigen (mock antigen) were used as specificity control. As shown in FIG. 12, HSV specific immunity was induced by ICP10ΔPK virus. The response was only 2–3 fold lower than that seen for HSV-2 under the same conditions.

EXAMPLE 15

ICP10ΔPK (CS) is More Attenuated than ICP10ΔPK (RF)

Because ICP10ΔPK (CS) appears to be more attenuated than ICP10ΔPK (RF) in cultured cells, we asked whether the same is also true in infected animals. We used the same mouse footpad model as used for ICP10ΔPK (RF). In order to at least partially compensate for the reduced growth of the ICP10ΔPK (CS) virus [relative to ICP10ΔPK (RF)] mice were injected with $1\times10^7$ pfu of virus and a proportional dose of HSV-2 was used as control. The titers of HSV-2 isolated from the footpads were not significantly higher than those seen in mice given $5\times10^6$ pfu (Example 12). By contrast, the titers of isolated ICP10ΔPK (CS) were lower than those of ICP10ΔPK (RF) and virus was only isolated for 3, as compared to 4, days p.i. The proportion of latently infected ganglia was 100% and 0% for HSV-2 as compared to ICP10ΔPK (CS) infected animals (Table 5).

TABLE 5

Growth and latency reactivation of ICP10ΔPK virus

| Virus | Mean virus titer in footpads[a] (pfu/ml) | | | Latency[c] (%) |
|---|---|---|---|---|
| | Day 2 | Day 3 | Day 4 | |
| HSV-2 | $5 \times 10^3$ (+)[b] | $4.1 \times 10^4$ (+) | $3.5 \times 10^7$ (+) | 10/10 (100) |
| ICP10ΔPK (CS) | $1.0 \times 10^3$ | $2.8 \times 10^2$ (+) | — | 0/10 (0) |

[a]Mice (n = 10) were infected with $1 \times 10^7$ pfu in the footpad. Virus titers were determined by plaque assay. Lesions were seen beginning on day 7 p.i. in HSV-2 infected mice.
[b]Ganglia were obtained on days 3 and 5 p.i., homogenized and assayed for virus. (+) means virus was isolated.
[c]Latency is no. of explanted ganglia positive for virus at 30 days p.i./no. tested
ND = not done

EXAMPLE 16

ICP10ΔPK (CS) protects from HSV-2 challenge better than ICP10ΔPK (RF)

We used the footpad model to examine protection by ICP10ΔPK (CS). The experiment was done as previously described for ICP10ΔPK (RF) except that the mice were immunized with 1×10 pfu of virus and they were given three immunizations (at 14–16 days intervals) before challenge with wild type HSV-2. Challenge was with $1 \times 10^8$ pfu of HSV-2 and it was done 3 weeks after the last immunization. All mice in the PBS group developed skin lesions from which virus was isolated, and 8/10 died on days 8–13 after challenge. By contrast, lesions were not seen and virus was not isolated from anyone of the immunized mice (Table 6). These findings indicate that the ICP10ΔPK (CS) virus has superior vaccine potential than the ICP10ΔPK (RF) virus in that it is somewhat more attenuated while providing superior protection. The latter is evidenced by the finding that virus was not isolated from any of the animals although the challenge was done with 10-fold higher titers of HSV-2 than those used for animals immunized with ICP10ΔPK (RF) where virus was isolated from 3/10 mice (Example 13).

TABLE 6

Protection mediated by ICP10ΔPK

| Immunization | Lesions | Challenge | Lesions (death) | Virus isolation |
|---|---|---|---|---|
| PBS | None | HSV-2 ($1 \times 10^8$) | 10/10 (8/10) | 10/10 |
| CP10ΔPK (CS) | None | HSV-2 ($1 \times 10^8$) | 0/10 (0/10) | 0/10 |

Mice (groups of 10) were immunized with PBS or ICP10ΔPK (3 sc injections) and challenged with HSV-2 in the footpad

EXAMPLE 17

ICP10ΔPK (CS) Virus Induces HSV-specific Immunity

A group of 3 mice was immunized with ICP10ΔPK (CS) ($1 \times 10^7$ pfu, 3 injections) as described in example 16. Two weeks after the last injection spleens were removed and T cells were used in lymphocyte proliferation assays done as in example 14. HSV-specific lymphoproliferation was seen in all animals. Proliferative levels (FIG. 13) were significantly higher than those seen before (FIG. 12), and approximately three-fold higher than those seen with the mitogen PHA. These findings indicate that ICP10ΔPK (CS) induces good levels of virus-specific T cell responses.

All references cited herein are incorporated by reference in their entirety.

While the invention has been described in detail, and with reference to specific embodiments thereof, it will be apparent to one with ordinary skill in the art that various changes and modifications can be made therein without departing from the spirit and scope thereof.

We claim:

1. A method of immunizing a subject against Herpes Simplex virus comprising the step: administering to the subject a vaccine comprised of Herpes Simplex Virus-2 ICP10ΔPK (CS) and a pharmaceutically acceptable carrier or diluent.

2. A method of conferring immunity against Herpes Simplex virus to a subject comprising administering the vaccine composition of claim 1.

3. A method of preventing clinical symptoms in a subject associated with Herpes Simplex Virus comprising administering the vaccine composition of claim 1.

4. The method of claim 1 wherein said subject is a human.

5. The method of claim 4 wherein the dosage range for said vaccine is 1–100 million pfu.

6. The method of claim 4 wherein said vaccine composition is administered via an intranasal, oral, intravaginal, subcutaneous or intradermal route.

7. The method of claim 2 wherein said subject is a human.

8. The method of claim 3 wherein said subject is a human.

9. The method of claim 1 wherein the dosage range for said vaccine is 1–100 million pfu.

10. The method of claim 2 wherein the dosage range for said vaccine is 1–100 million pfu.

11. The method of claim 3 wherein the dosage range for said vaccine is 1–100 million pfu.

12. The method of claim 7 wherein the dosage range for said vaccine is 1–100 million pfu.

13. The method of claim 8 wherein the dosage range for said vaccine is 1–100 million pfu.

14. The method of claim 1 wherein said vaccine composition is ad ministered via an intranasal, oral, intravaginal, subcutaneous or intradermal route.

15. The method of claim 2 wherein said vaccine composition is ad ministered via an intranasal, oral, intravaginal, subcutaneous or intradermal route.

16. The method of claim 3 wherein said vaccine composition is administered via an intranasal, oral, intravaginal, subcutaneous or intradermal route.

17. The method of claim 7 wherein said vaccine composition is administered via an intranasal, oral, intravaginal, subcutaneous or intradermal route.

18. The method of claim 8 wherein said vaccine composition is administered via an intranasal, oral, intravaginal, subcutaneous or intradermal route.

* * * * *